USOO5683688A

United States Patent [19]
Aggarwal et al.

[11] Patent Number: 5,683,688
[45] Date of Patent: Nov. 4, 1997

[54] UNGLYCOSYLATED RECOMBINANT HUMAN LYMPHOTOXIN POLYPEPTIDES AND COMPOSITIONS

[75] Inventors: Bharat B. Aggarwal, San Mateo; Patrick W. Gray, San Francisco, both of Calif.; Glenn E. Nedwin, Guilford, Conn.

[73] Assignee: Genentech, Inc., South San Francisco, Calif.

[21] Appl. No.: 836,765

[22] Filed: Feb. 14, 1992

Related U.S. Application Data

[60] Division of Ser. No. 732,312, May 9, 1985, abandoned, which is a continuation-in-part of Ser. No. 616,503, May 31, 1984, abandoned.

[51] Int. Cl.$^6$ .................. A61K 38/19; C07K 14/52; C07K 14/525
[52] U.S. Cl. ................. 424/85.1; 530/35.1; 435/69.5; 930/143
[58] Field of Search ................. 530/350, 395, 530/351; 930/140, 143; 435/69.5, 252.3, 252.33; 424/85.1

[56] References Cited

U.S. PATENT DOCUMENTS

| | | | |
|---|---|---|---|
| 4,481,137 | 11/1984 | Ohnishi et al. | 530/351 |
| 4,703,008 | 10/1987 | Lin | 435/240.2 |

FOREIGN PATENT DOCUMENTS

| | | | |
|---|---|---|---|
| 013828 | 6/1980 | European Pat. Off. | C12N 15/00 |
| 060057 | 9/1982 | European Pat. Off. | C12W 15/00 |
| 073656 | 3/1983 | European Pat. Off. | C12W 15/00 |
| 100641 | 2/1984 | European Pat. Off. | C12P 21/00 |
| 135797 | 8/1984 | European Pat. Off. | |
| 132125 | 1/1985 | European Pat. Off. | C07K 1/00 |
| 2534594 | 4/1984 | France | |
| 2106117 | 4/1983 | United Kingdom | C07G 7/00 |
| WO 85/04662 | 10/1985 | WIPO | C07G 7/100 |

OTHER PUBLICATIONS

Delente et al., "Glycosylation Revisited" *Trends in Biotech.* 3: 218 (1985).
Van Brunt, "Glycoprotein Remodeling, There's Nothing (Quite) Like The Real Thing," *Biotechnology* 4: 835–839 (1986).
Zoller et al., "Oligonucleotide–directed Mutagenesis Using M13–derived Vectors: An Efficient and General Procedure for the Production of Point Mutations in Any Fragment of DNA" *Nucl. Acids Res.* 10(20):6487–6500 (1982).
Proctor, J.C., et al (1982) *Clin. Res.* 30(1), p. 55A, "The Role of Glycosylation of Human Lymphotoxin in Cellular Destruction of Target Cells" (Meeting Abst.).
Klostergaard et al *Mol Immunol* 18(5) 1981, pp. 455–458.
Klostergaard et al, *Mol. Immunol* 18(12)1981, pp. 1049–1054.
Harris et al, *J. Immunol* 125(6) 1981, pp. 2165–2170.
Pichyangkul et al, Human Lymphokines, ed Khan et al, 1982, pp. 173–181.
Pichyangkul et al, *J. Clin Hematology & Oncology,* 1981, 11(4) p. 110.
Miyajima et al., "Analysis of Full–Length cDNA Clones Carrying GAL1 of *Saccharomyces cerevisiae:* A Model System for cDNA Expression," Nucleic Acids Research, 12: 6397–6414 (1984).
Mulligan et al., "Expression of a Bacterial Gene in Mammalian Cells," *Science* 209: 1422–1427 (1980).
Granger et al., *Cellular Responses to Molecular Modulators,* Mozes et al., ed., pp. 287–310 (1981).
Ruddle et al., *Lymphokine Research,* 21(1): 23–31 (1983).
Granger et al., *Biochemical Characterization of Lymphokines,* pp. 279–283 (1980).
Yamamoto et al., *J. Biol. Response Modifiers,* 3(1): 76–87 (1984).
Hiserodt et al., *Cell. Immunol.,* 26: 211 (1976).
Granger et al., *Cell. Immunol.,* 38: 388–402 (1978).
Walker et al., *J. of Immunol.,* 116(3): 807–815 (Mar. 1976).
Aggarwal et al., *J. Biol. Chem.,* 258(1): 686–691 (1984).
Rundell et al., *Immunopharm.,* 3: 9–18 (1981).
Granger et al., *Lymphokine Research,* 1(2): 45–49 (1982).
Gray et al., *Nature,* 312: 721–724 (1984).
Ransom et al., *Cancer Research,* 43: 5222–5227 (1983).
Toth et al., *Mol. Immunol.,* 18: 671–679 (1982).
Proctor et al., *Clin. Res.,* 30(1): 55A (1982).
Evans et al., *Cancer Immunol. Immunother.,* 12: 181–190 (1982).
Kull et al., *J. Immunol.,* 128(4): 1279–1283 (1981).
Sawada et al., *Japan J. Exp. Med.,* 46(4):263–267 (1976).
Lee et al., *Cell. Immunol.,* 48: 166–181 (1979).
De Weck et al., *Biochemical Characterization of Lymphokines,* pp. 279–312 (1980).
Papermaster et al., *Human Lymphokines,* Kahn et al., eds., pp. 459–477 (1982).
Aggarwal et al., Presentation at the 3rd Int. Lymphokine Workshop, Haverford, PA (Aug. 1–5, 1982).
Wallach et al., *The Biology of the Interferon System,* Demaeyer et al., eds., (1983).
Powell et al., *Lymphokine Research,* 4(1): 13–26 (1985).
Papermaster et al., *Cellular Responses to Molecular Modulators,* Mozes et al., eds., pp. 271–283 (1981).
Sawada et al., *Transplantation,* 18(4): 335–342 (1975).
Kornfeld & Kornfeld, *Ann. Rev. Biochem.,* 54:631–664 (1985).
Mathews et al., *Br. J. Cancer,* 42: 416–422 (1980).

(List continued on next page.)

*Primary Examiner*—David L. Fitzgerald
*Attorney, Agent, or Firm*—Diane L. Marschang

[57] ABSTRACT

Biologically active lymphotoxin polypeptides are synthesized in recombinant cell culture. Novel nucleic acid and vectors incorporating same are provided. The compositions and processes herein enable the economical preparation of compositions containing uniform lymphotoxin polypeptides and variant lymphotoxins having amino acid sequences that differ from those found in nature. The lymphotoxins are purified to a specific activity of $2$–$10\times10^7$ units/mg of protein by purification using a novel immobilized, lymphotoxin-neutralizing monoclonal antibody.

23 Claims, 16 Drawing Sheets

OTHER PUBLICATIONS

Neumann et al., *Biochem J.*, 184: 847–856 (1981).
Roberts, T. M., *Promoters Structure and Function*, Rodriguez et al., eds., pp. 452–461 (1982).
Ruddle et al., *Curr. Top. Microbiology Immun.*, 239–248 (1982).
Mercereau–Puijelon et al., *Expression of Eukaryotic Viral & Cellular Genes*, Petterson et al., eds., pp. 295–303 (1980).
Lane, Montague, *Cancer Diagnosis, Treatment and Prognosis*, Ackerman et al., eds. pp. 105–130 (1977).
Berman et al., *Trends in Biochem.*, 3(2): 51–53 (1985).
Knight et al., *J. Interferon Res.*, 2(3): 421–429 (1982).
Weitzen et al., *Cell. Immunol.*, 77:30–41 (1983).
Ransom et al., *Intl. J. Cancer*, 28:951–958 (1982).
Ransom et al., *JNCI*, 89(3): 741–744 (1982).
Ransom et al., *Intl. J. Cancer*, 32: 93–97 (1983).
Evans, *Cancer Immunol. Immunother.*, pp. 181–190 (1982).
Evans, *Cell. Immunol.* 76:295–303 (1983).
Ewans, *Immunopharmacology*, 3:347–359 (1981).
Khan et al., *Human Lymphokines*, pp.621–629 (1982).
Aggarwal et al., *IBC*, 258(1): 686–691 (1984).

Fig. 1A.

```
GAGGTTTATTGGGCCTCGGTCCTCCTCCTGCACCTGCTGCTGGATCCCCGGCCTGCCTGGGCCTGGGCCTTGGTTCTCCCC
1                                                  50 met thr pro pro glu
                                                                                    -30
                                                                    ATG ACA CCA CCT GAA
    arg leu phe leu pro arg val cys gly thr thr leu his leu leu leu gly leu leu val leu leu pro
                    -20                                         -10
    CGT CTC TTC CTC CCA AGG GTG TGT GGC ACC ACC CTA CAC CTC CTT CTG GGG CTG CTG GTT CTG CTG CCT
                        100                                         150 gly ala gln gly gly leu pro gly val gly leu thr pro ser ala ala gln thr ala arg gln his pro lys met his
                    1                           10                                          20
    GGG GCC CAG GGC CTC CCT GGT GTT GGC CTC ACA CCT TCA GCT GCC CAG ACT GCC CGT CAG CAC CCC AAG ATG CAT
                                            200 leu ala his ser thr leu lys pro ala ala his leu ile gly asp pro ser lys gln asn ser leu leu trp arg
                            30                              40
    CTT GCC CAC AGC ACC CTC AAA CCT GCT CAC CTC ATT GGA GAC CCC AGC AAG CAG AAC TCA CTG CTC TGG AGA
                    250                                         300 ala asn thr asp arg ala phe leu gln asp gly phe ser leu ser asn asn ser leu leu val pro thr ser gly
                    50                              60                              70
    GCA AAC ACG GAC CGT GCC TTC CTC CAG GAT GGT TTC TCC AGC AAC AAT TCT CTC CTG GTC CCC ACC AGT GGC
                        350                                         400 ile tyr phe val tyr ser gln val val phe ser gly lys ala tyr ser pro lys ala thr ser ser pro leu tyr
                            80                              90
    ATC TAC TTC GTC TAC TCC CAG GTG GTC TTC TCT GGG AAA GCC TAC TCT CCC AAG GCC ACC TCC TCC CCA CTC TAC
                    400                                 450 leu ala his glu val gln leu phe ser ser gln tyr pro phe his val pro leu leu ser ser gln lys met val
                    100                                 110                                 120
    CTG GCC CAT GAG GTC CAG CTC TTC TCC TCC CAG TAC CCC TTC CAT GTG CCT CTC CTC AGC TCC CAG AAG ATG GTG
                                        500
```

Fig. 2A-1

```
                                                              140
Tyr Pro Gly Leu Gln Glu Pro Trp Leu His Ser Met Tyr His Gly Ala Ala Phe Gln Leu Thr Gln Gly Asp Gln
TAT CCA GGG CTG CAG GAA CCC TGG CTG CAC TCG ATG TAC CAC GGG GCT GCG TTC CAG CTC ACC CAG GGA GAC CAG
550       PstI                                                                 600
              150                                160                       170
Leu Ser Thr His Thr Asp Gly Ile Pro His Leu Val Leu Ser Pro Ser Thr Val Phe Phe Gly Ala Phe Ala Leu
CTA TCC ACC CAC ACA GAT GGC ATC CCC CAC CTA GTC CTC AGC CCT AGT ACT GTC TTC TTT GGA GCC TTC GCT CTG
                                        650

STOP
TAG   AACTTGGAAAAAATCCAGAAAGAAAAAATAATTGATTTCAAGACCTTCTCCCCATTCTGCCTCCATTTCAGGGGTCGTCACCACCTC
                      700                                              750
      TCCTTTGGCCATTCCAACAGCTCAAGTCTTCCCTGATCAAGTCACCGGAGCTTTCAAAGAAGGAATTCTAGGCATCCCAGGGGACCCACACTCCCTGAAC
                      800                                              850    EcoRI
      CATCCCTGATGTCTGTCTGGCTGAGGATTTCAAGCCTGCCTAGGAATTCCCAGCCCAAAGCTGTTGGTCTTGTCCACCAGCTAGGTGGGGCCTAGATCCA
                      900                                              950
      CACACAGAGGAAGAGAGCAGGCACATGGAGGAGCTTGGGGGATGACTAGAGGCAGGAGGGGACTATTTATGAAGGCAAAAAATTAAATTATTTATTTATG
                      1000                                             1050
      GAGGATGGAGAGAGGGAATAATAGAAGAACATCCAAGGAGAAACAGAGACAGGCCCAAGAGATGAAGAGTGAGAGGGCATGCGCACAAGGCTGACCAAGA
                      1100                                             1150
      GAGAAGAAGTAGGAGGCATGAGGGATCACAGGGCCCCAGAAGGCAGGAAAGGCTCTGAAAGCCAGCTGCCGACCAGAGCCCCACACGGAGGCATCTGCACC
                      1200                                             1250
      CTCGATGAAGCCCAATAAACCCTCTTTTCTCTGAAAAAAAAAAAAA    3'
                      1300
```

Fig. 2A-2

HOMOLOGY OF HUMAN, MURINE AND BOVINE LYMPHOTOXIN

```
              -34  -30
HUMAN         met thr pro pro glu arg phe leu pro arg val cys gly
MURINE        met thr leu gly arg arg leu his leu leu arg val leu gly
BOVINE        met thr pro pro gly arg ser leu pro pro ser val gln his
CONSENSUS     met thr                              arg                  val -20                                                 -10                              10
HUMAN         thr thr leu his leu leu leu leu gly leu leu leu val leu leu pro
MURINE                        val phe leu leu gly leu leu leu ala leu pro leu
BOVINE        pro pro         leu leu leu leu gly leu leu leu pro met pro leu
CONSENSUS     pro pro         leu leu leu leu     leu leu leu 1                                                          10
HUMAN         gly ala gln gly LEU PRO GLY VAL GLY LEU THR PRO SER ALA
MURINE        gly ala gln     LEU SER GLY VAL ARG PHE         SER ALA
BOVINE        glu ala gln gly LEU ARG GLY ILE GLY LEU THR PRO SER ALA
CONSENSUS         ala gln     LEU     GLY                             SER ALA 20
HUMAN         ALA GLN THR ALA ARG GLN HIS PRO LYS MET HIS LEU ALA HIS SER THR
MURINE        ALA ARG THR ALA HIS PRO LEU PRO GLN LYS HIS LEU THR HIS GLY ILE
BOVINE        ALA GLN PRO ALA HIS GLN GLN LEU PRO THR PRO PHE THR ARG GLY THR
CONSENSUS     ALA
```

*Fig. 4A*

|  | | | | 30 | | | | | 40 | | | |
|---|---|---|---|---|---|---|---|---|---|---|---|---|
| HUMAN | LEU | LYS | PRO | ALA | ALA | HIS | LEU | ILE | GLY | ASP | PRO | SER | LYS | GLN |
| MURINE | LEU | LYS | PRO | ALA | ALA | HIS | LEU | LEU | VAL | GLY | TYR | PRO | SER | LYS | GLN |
| BOVINE | LEU | LYS | PRO | ALA | ALA | HIS | LEU | LEU | VAL | ASP | PRO | SER | ASN | PRO |
| CONSENSUS | LEU | LYS | PRO | ALA | ALA | HIS | LEU | | | GLY | | PRO | SER | |

|  | | | | | 50 | | | | | | | | |
|---|---|---|---|---|---|---|---|---|---|---|---|---|---|
| | ASN | SER | LEU | LEU | TRP | ARG | ALA | ASN | THR | ASP | ARG | ALA | PHE | LEU | GLN | ASP |
| | ASN | SER | LEU | LEU | TRP | ARG | ALA | ASN | ALA | ASP | ARG | ALA | PHE | LEU | ARG | HIS |
| | ARG | THR | LEU | THR | LEU | ARG | ALA | ASN | THR | ASP | ARG | ALA | PHE | LEU | PRO | THR |
| | | | LEU | | | ARG | ALA | ASN | | ASP | ARG | ALA | PHE | LEU | |

|  | | | | 60 | | | | | 70 | | | | |
|---|---|---|---|---|---|---|---|---|---|---|---|---|---|
| HUMAN | GLY | PHE | SER | LEU | SER | ASN | ASN | SER | LEU | VAL | PRO | THR | SER |
| MURINE | GLY | PHE | SER | LEU | SER | ASN | ASN | SER | LEU | ILE | PRO | THR | SER |
| BOVINE | ALA | PHE | SER | LEU | SER | ASN | ASN | SER | LEU | VAL | PRO | THR | SER |
| CONSENSUS | | PHE | SER | LEU | SER | ASN | ASN | SER | LEU | | PRO | THR | SER |

|  | | | | 80 | | | | | | | | | |
|---|---|---|---|---|---|---|---|---|---|---|---|---|---|
| HUMAN | GLY | ILE | TYR | PHE | VAL | TYR | SER | GLN | VAL | VAL | PHE | SER | GLY | LYS | ALA | TYR |
| MURINE | GLY | LEU | TYR | PHE | VAL | TYR | SER | GLN | VAL | VAL | PHE | SER | GLY | GLU | SER | CYS |
| BOVINE | GLY | LEU | TYR | PHE | VAL | TYR | SER | GLN | VAL | VAL | PHE | SER | GLY | ARG | GLY | CYS |
| CONSENSUS | GLY | | TYR | PHE | VAL | TYR | SER | GLN | VAL | VAL | PHE | SER | GLY |

Fig. 4B

```
                          90                              100
HUMAN       SER PRO LYS ALA THR SER SER PRO LEU TYR LEU ALA HIS GLU
MURINE      SER PRO ARG ALA ILE PRO THR PRO ILE TYR LEU ALA HIS GLU
BOVINE      PHE PRO ARG ALA THR PRO THR PRO LEU TYR LEU ALA HIS GLU
CONSENSUS       PRO     ALA                 PRO     TYR LEU ALA HIS GLU

110
VAL GLN LEU PHE SER SER GLN TYR PRO PHE HIS VAL PRO LEU LEU LEU SER
VAL GLN LEU PHE SER SER GLN TYR PRO PHE HIS VAL PRO LEU LEU LEU SER
VAL GLN LEU PHE SER PRO GLN TYR PRO PHE HIS VAL PRO LEU LEU LEU SER
VAL GLN LEU PHE SER     GLN TYR PRO PHE HIS VAL PRO LEU LEU LEU SER 120                              130
HUMAN       SER GLN LYS MET VAL TYR PRO GLY LEU GLN GLU PRO TRP LEU
MURINE      ALA GLN LYS SER VAL TYR PRO GLY LEU GLN GLY PRO TRP VAL
BOVINE      ALA GLN LYS SER VAL CYS PRO GLY PRO GLY ARG TRP VAL
CONSENSUS       GLN LYS     VAL     PRO GLY     GLN         TRP

140
HIS SER MET TYR HIS GLY ALA ALA PHE GLN LEU THR GLN GLY ASP GLN
ARG SER MET TYR GLN GLY ALA VAL PHE LEU LEU SER LYS GLY ASP GLN
ARG SER VAL TYR GLN GLY ALA VAL PHE LEU LEU THR ARG GLY ASP GLN
SER     TYR     GLY ALA     PHE LEU                 GLY ASP GLN
```

*Fig. 4C*

```
                              150                     160
HUMAN       LEU SER THR HIS THR ASP GLY ILE PRO HIS LEU VAL LEU SER
MURINE      LEU SER THR HIS THR ASP GLY ILE SER HIS LEU HIS PHE SER
BOVINE      LEU SER THR HIS THR ASP GLY ILE SER HIS LEU LEU LEU SER
CONSENSUS   LEU SER THR HIS THR ASP GLY ILE     HIS         LEU SER

170
            PRO SER THR VAL PHE PHE GLY ALA PHE ALA LEU
            PRO SER SER VAL PHE PHE GLY ALA PHE ALA LEU
            PRO SER SER VAL PHE PHE GLY ALA PHE ALA LEU
            PRO SER     VAL PHE PHE GLY ALA PHE ALA LEU
```

*Fig. 4D*

UNGLYCOSYLATED RECOMBINANT HUMAN LYMPHOTOXIN POLYPEPTIDES AND COMPOSITIONS

This is a divisional of prior application Ser. No. 06/732,312, filed 9 May 1985 and now abandoned, which is in turn a continuation-in-part of application Ser. No. 06/616,503, filed 31 May 1984, now abandoned. Reference is made to related application Ser. No. 06/608,316 entitled "Human Lymphotoxin", filed 7 May 1984 and now abandoned, and to application Ser. No. 06/616,502 entitled "Anti-Lymphotoxin", filed 31 May 1984, now U.S. Pat. No. 4,959,457.

BACKGROUND

This application relates to lymphokines. In particular, it relates to lymphotoxin and derivatives thereof.

Lymphotoxin was first identified as a biological factor with anticellular activity on neoplastic cell lines. An activity identified as lymphotoxin and obtained from mitogen-stimulated lymphocytes is associated with a spectrum of cytotoxic activities ranging from cytostasis of certain tumor cell lines to marked cytolysis of other transformed cells. However, lymphotoxin activity is characterized by little or no anticellular activity on primary cell cultures and normal cell lines tested. This putative discriminating anticellular property of lymphotoxin led to in vivo studies which suggest that lymphotoxin may have a potent antitumor activity.

Lymphotoxin is the term applied to what has been described as a family of molecules. Lymphotoxin molecules have been identified as glycoproteins divided into five molecular weight classes, each of which in turn is heterogenous with respect to charge. The human alpha (MW 70–90,000) and beta (MW 25–50,000) classes appear to predominate in most lymphocyte supernatants. The alpha MW classes can be separated by charge into at least seven subclasses, while the beta subclass has been separated into two distinct subclasses (G. Granger et al. in Mozes et al., Ed., 1981, *Cellular Responses to Molecular Modulators* pp 287–310). Also identified have been complex (MW>200,000) and gamma (MW 10–20,000) lymphotoxin forms. The various lymphotoxin forms and classes differ from one another in their stability and kinetics of appearance in culture. Furthermore, they may aggregate together with the complex class under conditions of low ionic strength. The lower molecular weight classes of lymphotoxins have been disclosed to be relatively unstable and weakly cell lytic compared to the higher molecular weight classes (Hiserodt et al., 1976, "Cell. Immun." 26: 211; Granger et al. in De Weck et al. Ed., 1980 *Biochemical Characterization of Lymphokines* pp 279–283). Gamma class activity has not been studied extensively because of its instability (G. Granger et al., 1978 "Cellular Immunology" 38: 388–402). The beta class also has been reported to be unstable (Walker et al., "J. of Immun." 116[3]: 807–815 [March 1976]).

It should be understood that lymphokine terminology is not uniform. At present, the names given to cell culture products are largely a function of the cells which are believed to elaborate the product and the performance of the products in biological assays. However, these products remain poorly characterized in large measure because many studies have been conducted with partially pure preparations and because the assays used to characterize the products are not molecule-specific and in any case are subject to considerable variation. The true identity of the various cytotoxic factors will remain unknown in the absence of standard terminology based on clearly assayable distinguishing characteristics such as 35 amino acid sequences or immune epitopes. As examples of other names given to cytotoxic cell culture products are tumor necrosis factor, NK cell cytotoxic factor, hemorrhagic necrosis factor and macrophage cytotoxin or cytotoxic factor.

Copending and commonly assigned U.S. Ser. No. 608,316, filed May 7, 1984, now abandoned and EP 100,641A (published Feb. 15, 1984) describe amino acid sequences for a human lymphotoxin isolated from the human lymphoblastoid cell line RPMI-1788.

Hayashi et al., EP 132,125A (published Jan. 23, 1985) describe recovering a protein from a rabbit following stimulation of its reticuloendothelial system. The protein was reported to have antitumor activity and the N-terminal amino acid sequence Ser-Ala-Ser-Arg-Ala-Leu-Ser-Asp-Lys-Pro-Leu-Ala-His-Val-Val-Ala-Asn-Pro-Gln-Val-Glu-Gly-Gln-Seu-Gln-Trp-Leu.

Copending and commonly assigned U.S. Ser. No. 628,059, filed Jul. 5, 1984 and now abandoned, discloses the purification and recombinant synthesis of a cytotoxic human polypeptide identified as tumor necrosis factor and having the N-terminal amino acid sequence Val-Arg-Ser-Ser-Ser-Arg-Thr-Pro-Ser-Asp-Lys-Pro-Val-Ala-His-Val-Val-Ala-Asn-Pro.

Ohnishi et al. (U.S. Pat. No. 4,481,137) discloses obtaining a 7–9,000 MW substance named $CB_{x3}$ from BALL-1 cell culture that suppresses the growth of tumor cells and that has an Ala-Ala N-terminus.

According to Toth and Granger, "Mol. Immun." 16: 671–679 (1979), neither the removal of sialic acid from lymphotoxin-containing lymphocyte supernatants by neuraminodase treatment nor the addition of N-acetyl-glucosamine, galactose, lactose, mannose, α-methyl-mannoside or fucose to the supernatants had any affect on in vitro lytic activity. Toth et al. thus concluded that simple sugars do not appear to play a role in the activity of their lymphotoxin. However, Toth et al. also observe that saccharides play an important role in the action of other lymphokines and concluded that they could not exclude the participation of more complicated forms of oligo saccharides in the cytotoxic activity of lymphotoxin.

Subsequently, Proctor, Klostergaard and Granger ("Clinical Research", 1982, 30(1): 55A) reported that human lymphocytes, when activated by PHA in the presence of tunicamycin (to inhibit the addition of N-linked carbohydrate moieties to lymphotoxin molecules), released biologically inert lymphotoxin. According to these authors, immunochemical studies revealed that while the carbohydrate moiety of lymphotoxin was not needed for its transport and release by the activated lymphocyte into the supernatant, the carbohydrate was needed in order to have effective target cell destruction because the carbohydrate was responsible for the appropriate conformation of the lymphotoxin molecule(s).

Other literature that should be studied in connection with this application includes Evans, "Cancer Immunol. Immunother." 12: 181–190 (1982); Lee et al., "Cell. Immun." 48: 166–181 (1979); De Weck et al. Ed., (1980) *Biochemical Characterization of Lymphokines* pp 279–312; Khan et al. Ed. (Jun. 30, 1982) *Human Lymphokines* pp 459–477; Aggarwal et al., Presentation at the 3rd International Lymphokine workshop in Haverford, Pa., Aug. 1–5 1982; Ransom et al., "Cancer Research" 43: 5222–5227 (November 1983); Kull et al., "J. of Immun." 126(4): 1279–1283 (April 1981); J. Sawada, et al., "Jpn. J. Exp. Med." 46: 263–267

(1976); G. Granger et al., "Cell Immunol" 38:388–402 (1978); J. Rundell et al., "Immunopharmacology" 3: 9–18 (1981); G. Granger et al., "J. Lymphokine Res."1: 45–49 (1982); N. Ruddle et al., "Lymphokine Res." : 23–31 (1983); M. Mitsuhashi et al., U.K. Patent Application 2,106,117; H. Enomoto, European Patent Application 87,087A; B. Williamson et al., "P.N.A.S. USA" 80:5397–5401 (1983) and S. Wright et al., "J. Immunol" 126: 1516–1521 (1981)

The lymphotoxin (or substances identified as lymphotoxin) obtained heretofore from lymphocyte culture are present in low concentrations, on the order of 0.05–2× $10^6$ units/l in supernatants of RPMI-1788 cells or primary lymphocytes. The amounts harvested often vary considerably, and primary lymphocytes are expensive. An economical method for producing lymphotoxin is needed (Yamamoto et al., "J. of Biological Response Modifiers" 3:[1] 76–87 [1984]).

Prior methods also fail to produce lymphotoxin which is homogeneous as to amino acid sequence, an important feature for drug utilities. Lymphotoxin recovered from cell line culture exhibits amino terminal heterogeneity, probably due to proteolytic processing (see the above cited U.S. Ser. No. 608,316 filed May 7, 1984, now abandoned). Cultures of primary lymphocytes, e.g. from adenoids or peripheral blood, must necessarily contain the cells of many donors for reasons of economy. However, the products of these cells will reflect genetic variation among the donors so that the resulting "lymphotoxin" may in fact be a mixture of allelic species. Obviously, the proportions and identities of such alleles will be unknown from lot-to-lot. A method is needed for producing lymphotoxin that is uniform as to its amino acid sequence.

Prior methods also are limited to the production of lymphotoxin having amino acid sequences corresponding to those found in nature. Substituting, deleting or inserting different amino aids in these sequences would require extensive and costly chemical modifications, if such could be accomplished at all. Methods are needed for easily introducing variations into the amino acid sequences of lymphotoxin.

Although the antitumor effects and apparent therapeutic value of lymphotoxin activity have been reported in the literature since 1968, lymphotoxin has not been studied in extensive clinical protocols or commercialized due to the small quantities and heterogenous nature of the lymphotoxin made available through prior methods. Methods are needed to economically prepare quantities of lymphotoxin adequate for clinical studies.

Rabbit antisera have been described in the literature which are capable of neutralizing the cytolytic activity of various cytotoxins, including substances identified as lymphotoxin (Yamamoto et al. "Cell. Immun." 38: 403–416 (1978); Gately et al., "Cell. Immun." 27: 82–93 (1976); Hiserodt et al., "J. of Immun." 119(2): 374–380 (1977); Zacharchuk et al., "P.N.A.S. USA" 80: 6341–6345 (October 1983); Ruddle et al., "Lymphokine Research" 2(1) 23–31 (1983); Mannel et al., "Infection and Immunity" 33(1): 156–164 (1981); Wallach et al. E. De Maeyer et al. Ed. *The Biology of the Interferon System* pp 293–302 (Pub. September 1983) and Stone-Wolff et al., "J. Exp. Med." 159: 828–843 (March 1984). Since this antiserum is polyclonal it contains a multiplicity of antibodies directed against the immunogen lymphotoxin. Any one or more of these antibodies is acting to neutralize the "lymphotoxin" activity. Further, the literature reports generally are unclear as to the molecular identity of the substance responsible for lymphotoxin activity that was used as the immunogen. What is needed for diagnosis and immunoaffinity purification procedures is a monospecific antibody directed against a clearly and unambiguously identified lymphotoxin molecule. It is an objective of this invention to provide such an antibody.

It is a further object herein to provide methods for economically synthesizing a lymphotoxin form in a composition wherein the amino acid sequence of substantially all of the lymphotoxin molecules is the same.

It is another object to produce predetermined variations in the amino acid sequence of a lymphotoxin form, more specifically, amino acid deletions, insertions, substitutions, or combinations thereof.

SUMMARY OF THE INVENTION

The objectives of this invention have been accomplished by the successful recombinant expression of protein having lymphotoxin activity. This lymphotoxin species, which is described herein in terms of its activity and natural or variant amino acid sequence, is henceforth referred to as lymphotoxin. Surprisingly, the DNA encoding lymphotoxin has been identified notwithstanding the minute levels of lymphotoxin expressed in homologous cells and uncertainty as to the time at which messenger RNA encoding lymphotoxin appears in homologous cells. Also surprisingly, biologically active lymphotoxin is expressed in recombinant cells that do not glycosylate the lymphotoxin (or that would not be expected to do so in the same fashion as homologous cells) and the lymphotoxin so expressed is recovered having a substantially uniform amino acid sequence, without N-terminal enzymatic hydrolysis. DNA encoding lymphotoxin is expressed in cell cultures in copious quantities exceeding 0.1 to $1 \times 10^{11}$ units/liter of culture lysate.

The lymphotoxin that is expressed by a recombinant host cell will depend upon the DNA employed to encode the lymphotoxin or its precursors as well as upon the host cell selected. The nucleic acid sequences employed herein for lymphotoxin synthesis are novel. They are characterized by nucleotide sequences that differ from the native or natural sequence in one or more of the following ways: The DNA is free of introns, in the case of human lymphotoxin the intron present between nucleotides 284 and 285 (FIG. 2a); the DNA is free of nucleic acid encoding other proteins of the organism from which the DNA originated; the nucleic acid encoding lymphotoxin is ligated into a vector; and/or the nucleic acid is capable of hybridizing to nucleic acid encoding lymphotoxin provided, however, that such hybridizing nucleic acid does not have the nucleotide sequence of natural DNA or RNA encoding lymphotoxin.

Mutant nucleic acids encoding lymphotoxin are the product of recombinant manipulations. Silent mutations in the 5' untranslated or translated nucleic acid for lymphotoxin are provided in order to enhance expression levels in selected hosts, e.g. by reducing the probability of stem-and-loop messenger RNA structures in the 5' regions of the nucleic acid, or by substituting host-preferred codons for those found in natural nucleic acid isolates.

Mutations in the nucleic acids which are expressed rather than silent enable the preparation of lymphotoxin species having the amino acid sequence of native lymphotoxin or primary sequence variants thereof with amino acid sequences differing from the native lymphotoxin. The mutant lymphotoxin is recovered as such or is further processed by the host cell to obtain the desired lymphotoxin species.

These nucleic acids or nucleic acids that hybridize therewith, or fragments thereof, are labelled and used in hybridization assays for the identification or determination of genetic material encoding lymphotoxin.

In processes for the synthesis of lymphotoxin, DNA which encodes lymphotoxin is ligated into a vector, the vector used to transform host cells, the host cells cultured and lymphotoxin recovered from the culture. This general process is used to synthesize lymphotoxin having the amino acid sequence of native lymphotoxin or to construct novel lymphotoxin variants, depending upon vector construction and the host cell chosen for transformation. The lymphotoxin species which are capable of synthesis herein include leucyl amino-terminal lymphotoxin, histidyl amino-terminal lymphotoxin, pre lymphotoxin, and lymphotoxin variants including (a) fusion proteins wherein a heterologous protein or polypeptide is linked by a peptide bond to the amino and/or carboxyl-terminal amino acids of lymphotoxin, (b) lymphotoxin fragments, especially fragments of pre lymphotoxin in which any amino acid between −34 and +23 is the amino-terminal amino acid of the fragment, (c) lymphotoxin mutants wherein one or more amino acid residues are substituted, inserted or deleted, (d) methionyl or modified methionyl (such as formyl methionyl or other blocked methionyl species) amino-terminal derivatives, and/or (e) unglycosylated or variantly glycosylated species of all of the foregoing.

If a mammalian cell is transformed with nucleic acid encoding lymphotoxin operably ligated to a eucaryotic secretory leader (including the native lymphotoxin secretory leader), or if nucleic acid which encodes lymphotoxin is operably ligated in a vector to a procaryotic or yeast secretory leader which is recognized by the host cell to be transformed (usually the organism from which the leader sequence was obtained), the host transformed with the vector and cultured, then nonmethionylated amino terminal lymphotoxin species ordinarily are recovered from the culture.

If DNA encoding lymphotoxin is operably ligated into a vector without a secretory leader sequence and then used to transform a host cell, the lymphotoxin species which are synthesized are generally substituted with an amino-terminal methionyl or modified methionyl residue such as formyl methionyl.

Methods are provided whereby in vitro mutagenesis of the nucleic acid encoding lymphotoxin leads to the expression of lymphotoxin variants not heretofore available. First, N-terminal methionyl or modified methionyl lymphotoxin is expressed by host cells transformed with nucleic acid encoding lymphotoxin which is directly expressed, i.e., which is not operably linked to a secretory leader sequence.

Secondly, in vitro, site-specific, predetermined or random mutagenesis is employed to introduce deletions, substitutions and/or insertions into the nucleic acid that encodes lymphotoxin. Lymphotoxin fusions are produced in this manner. The lymphotoxin derivatives obtained upon expression of mutant nucleic acid exhibit modified characteristics.

Finally, unglycosylated or variantly glycosylated lymphotoxins are provided as novel lymphotoxin species. Unglycosylated lymphotoxin is produced by prokaryotic expression of DNA encoding lymphotoxin. Variantly glycosylated lymphotoxin species are the product of recombinant culture in transformed higher eukaryotic, ordinarily mammalian, cells.

The lymphotoxin produced herein is purified from culture supernatants or lysates by immunoaffinity adsorption using insolubilized lymphotoxin-neutralizing antibody. This antibody, which is most efficiently produced in monoclonal cell culture, is raised in mice by immunization with alum-adsorbed lymphotoxin.

The lymphotoxin of this invention is combined for therapeutic use with physiologically innocuous stabilizers and excipients and prepared in sterile dosage form as by lyophilization in dosage vials or storage in stabilized aqueous preparations. Alternatively, the lymphotoxin is incorporated into a polymer matrix for implantation into tumors or surgical sites from which tumors have been excised, thereby effecting a timed-release of the lymphotoxin in a localized high gradient concentration.

The therapeutic compositions herein are administered in therapeutically effective doses by implantation, injection or infusion into animals, particularly human patients, that bear malignant tumors.

BRIEF DESCRIPTION OF THE DRAWINGS

Figure 1A:
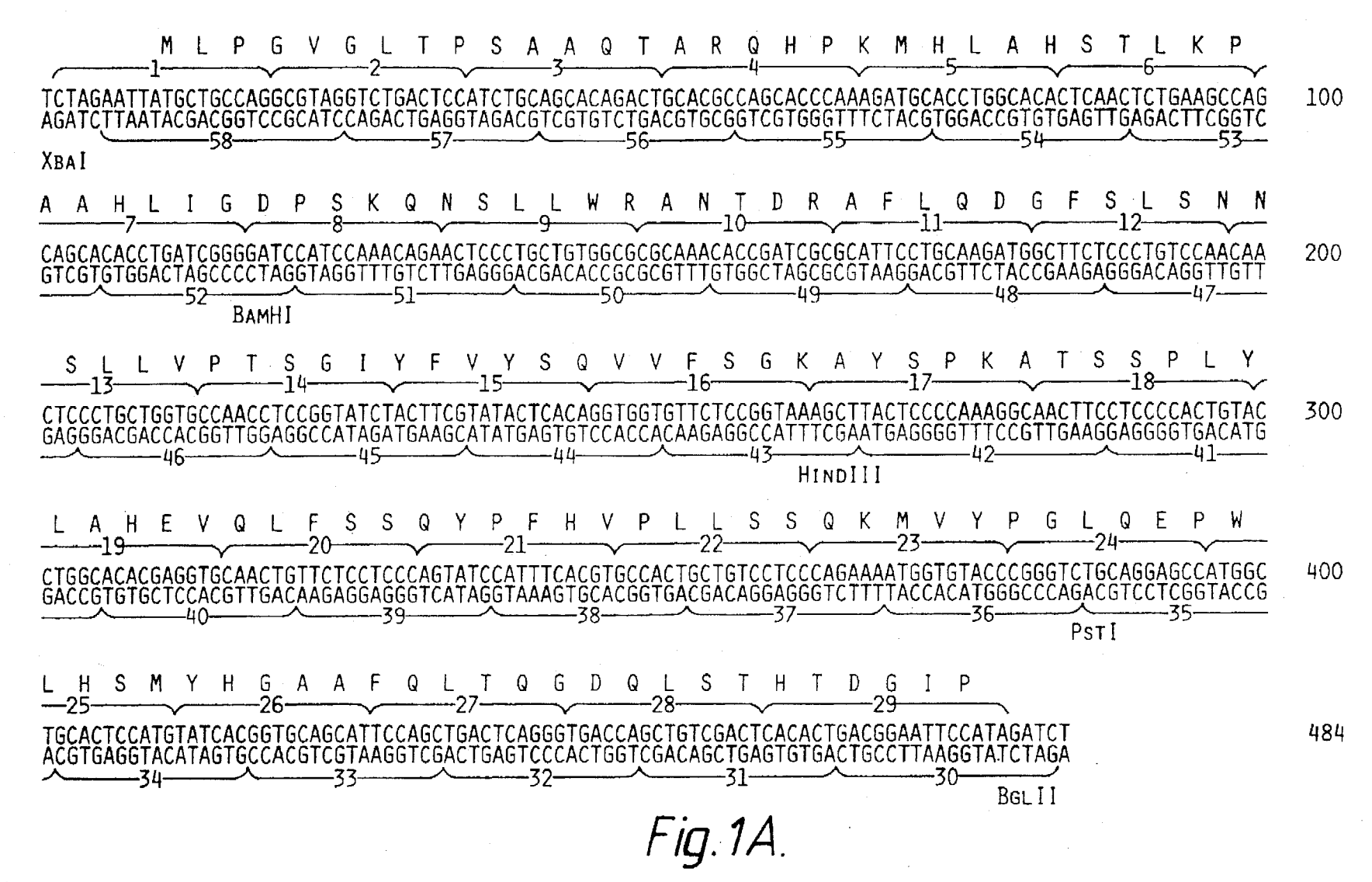

FIG. 1a depicts a DNA sequence and its putative amino acid sequence encoding a lymphotoxin fragment.

FIGS. 1b-I and 1b-II demonstrate the construction of synthetic DNA encoding the FIG. 1a fragment.

FIGS. 2a-I and 2a-II show the complete amino acid sequence for pre lymphotoxin, its coding DNA plus 5' and 3' flanking untranslated regions.

FIG. 2b illustrates a method of constructing an expression vector for methionyl leucyl amino-terminal lymphotoxin and its amino terminal methionyl derivatives.

FIGS. 4-I through 4-IV depict the amino acid sequences for human, murine and bovine lymphotoxin, and the consensus mammalian lymphotoxin residues.

FIGS. 5a-I, 5a-II, 5b-I, and 5b-II depict the construction of a plasmid encoding a fusion of lymphotoxin and a bacterial signal sequence.

DETAILED DESCRIPTION

Lymphotoxin is defined for the purposes of this application as a biologically active polypeptide having a region demonstrating substantial structural amino acid homology with at least a portion of the lymphotoxin amino acid sequence shown in FIGS. 2a-I and 2a-II. Biological activity is defined as preferential, cytotoxic activity as defined below, immunological cross-reactivity with a cytotoxic lymphotoxin or the ability to compete with cytotoxic lymphotoxin for lymphotoxin cell surface receptors. In the latter two instances the lymphotoxin need not be cytotoxic per se. Immunologically cross-reactive mutants are useful as immunogens for raising anti-lymphotoxin in animals, e.g. for the preparation of immunoassay reagents, while non-cytotoxic competitive mutants find utility as labelled reagents in competitive-type immunoassays for biologically active lymphotoxin.

Preferential cytotoxic activity is defined as the preferential destruction or growth inhibition of tumor cells in vivo or in vitro when compared to normal cells under the same conditions. Destruction of tumor cells by lysis in vitro or necrosis in vivo is the preferred assay endpoint, although cytostasis or antiproliferative activity also is used satisfactorily.

Suitable assays for detecting the anticellular activities of lymphotoxin are described in B. Aggarwal, et al., 1984, "J. Biol. Chem." 259 (1), 686–691 and E. Carswell, et al., 1975, "Proc. Natl. Acad. Sci. USA" 72, 3666–3670.

Lymphotoxin specific activity is defined herein in terms of target cell lysis, rather than cytostasis. One unit of lymphotoxin is defined as the amount required for 50 percent lysis of target cells plated in each well as is further described in Example 1. However, other methods for determining cytotoxic activity are acceptable.

Figures 1, 1B:
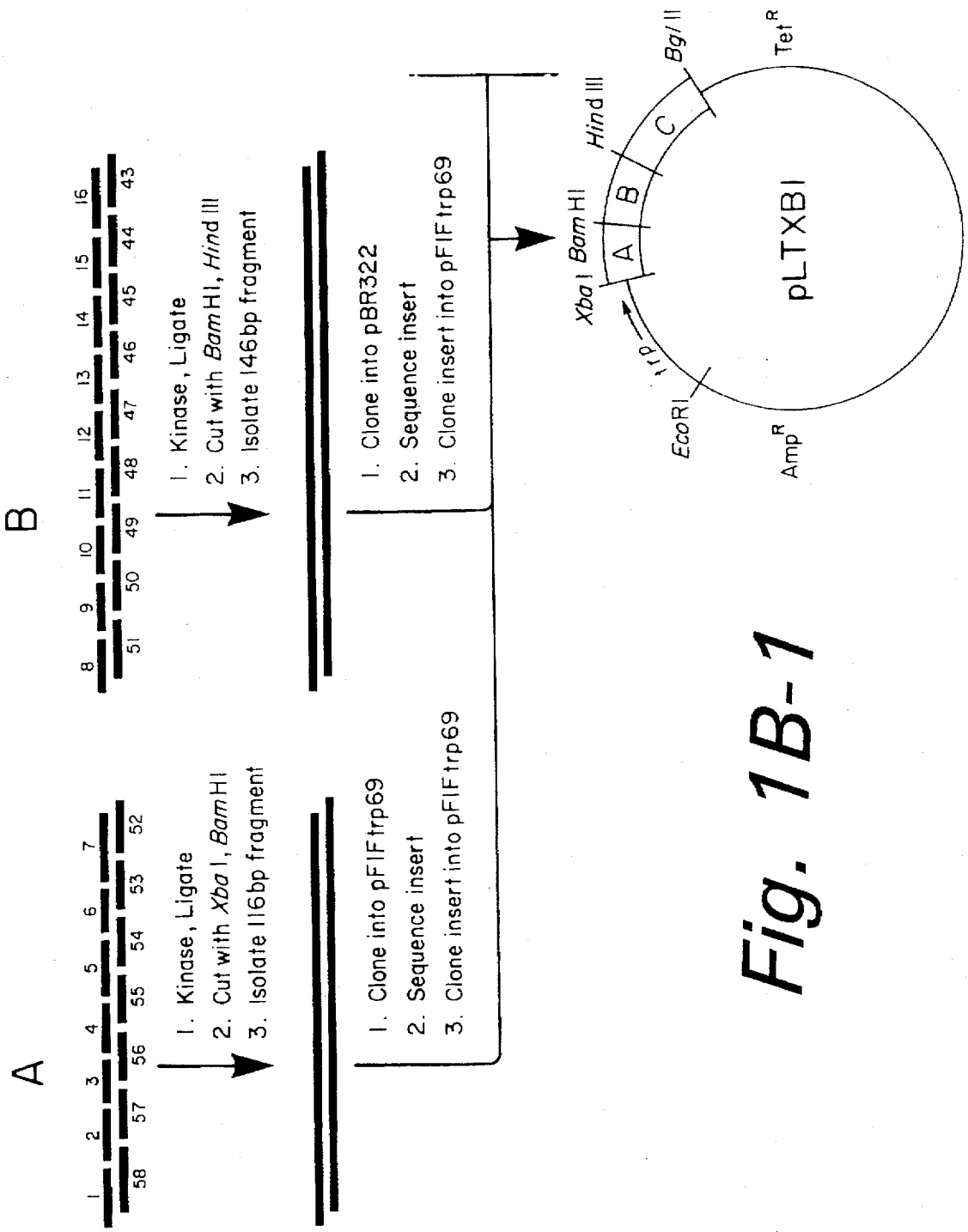
Figures 1, 1B, 2:
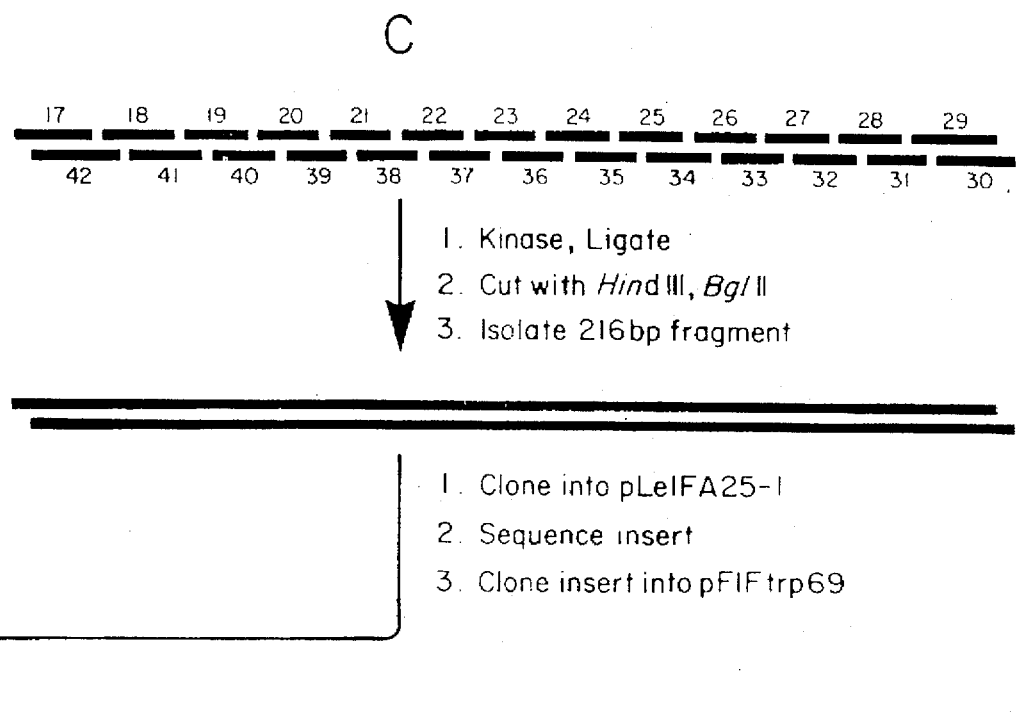

Substantial structural homology generally means that greater than about 60 percent, and usually greater than about 70 percent of the amino acid residues in the polypeptide are the same or conservative substitutions for the corresponding residue(s) in the sequence of FIG. 2a.

Not all of the sequence of a lymphotoxin polypeptide need be homologous with the FIGS. 2a-1/2a2 sequence. Only a portion thereof need be homologous with any portion of the FIG. 2a sequence so long as the candidate exhibits the required biological activity. Generally, homology should be demonstrable for regions of about from 20 to 100 amino acid residues, recognizing that occasional gaps may need to be introduced in order to maximize the homology.

Less homology is required for polypeptides to fall within the definition if the region of homology with the FIGS. 2a-I/2a-II sequence is not in one of the lymphotoxin key regions, i.e. regions that are important for cytotoxic activity. The key regions of the FIGS. 2a-I/2a-II sequence are believed to be about residues 162–171, 52–83 and 127–148.

Lymphotoxin is defined to specifically exclude human tumor necrosis factor or its natural animal analogues (D. Pennica et al., "Nature" 312:20/27 December, 1984, pp. 724–729 and B. Aggarwal et al., "J. Biol. Chem." 260[4]: 2345–2354 [1985]).

Structurally similar refers to dominant characteristics of the amino acid side chains such as basic, neutral or acid, hydrophilic or hydrophobic, or the presence or absence of steric bulk. Substitution of one structurally similar amino acid for another generally is known in the art as a conservative substitution.

A significant factor in establishing the identity of a polypeptide as lymphotoxin is the ability of antisera which are capable of substantially neutralizing the cytolytic activity of substantially homogeneous, lymphoblastoid (or natural) lymphotoxin to also substantially neutralize the cytolytic activity of the polypeptide in question. However it will be recognized that immunological identity and cytotoxic identity are not necessarily coextensive. A neutralizing antibody for the lymphotoxin of FIGS. 2a-I/2a-II may not bind a candidate protein because the neutralizing antibody happens to be directed to a site on lymphotoxin that merely neighbors a region that is critical to lymphotoxin cytotoxic activity, but which acts as a neutralizing antibody by steric hinderance of the lymphotoxin active site. A candidate protein mutated in this innocuous region might no longer bind the neutralizing antibody, but it would nonetheless be lymphotoxin in terms of substantial homology and biological activity.

Lymphotoxin obtained by culture of lymphoblastoid cell lines has been determined to have the following characteristics: A molecular weight of 20,000 or 25,000, depending upon the degree of glycosylation and N-terminal heterogeneity; glycosylation at Asn+62 (FIG. 2a); a tendency to aggregate, particularly to organize into multimers; an isoelectric point of about 5.8; pH lability (a loss of >50 percent of cytolytic activity when stored for 24 hours in ammonium bicarbonate buffer at 10 µg/ml concentration with pH levels less than about 5 or greater than about 10); and substantial losses in activity upon incubation in aqueous solution for 5 min. at 80° C. Two lymphoblastoid lymphotoxin molecular weight species have been identified. The 25,000 da species of lymphoblastoid lymphotoxin has an amino-terminal leucine residue. Polypeptides having the amino acid sequence of the 25,000 da species are called leucyl amino-terminal lymphotoxin. The 20,000 da species of lymphoblastoid lymphotoxin is characterized by an amino-terminal histidine and corresponding sequences are termed histidyl amino-terminal lymphotoxin. It is important to observe that these characteristics describe the native or wild type human lymphotoxin obtained from lymphoblastoid cell cultures. While lymphotoxin as defined herein includes native, glycosylated lymphotoxin, other related cytotoxic polypeptides many fall within the scope of the definition. For example, the glycosylation ordinarily associated with an animal lymphotoxin may be modified upon expression in a heterologous recombinant eukaryotic host cell, thereby bringing the modified lymphotoxin outside of the molecular weights or isoelectric point established for human lymphoblastoid lymphotoxin. Lymphotoxin which is entirely unglycosylated is produced in recombinant bacterial culture with its molecular weight, isoelectric point and other characteristics correspondingly modified. In addition, post-translational processing of pre lymphotoxin from a first animal species in a cell line derived from another animal species may result in a different amino-terminal residue than is ordinarily the case for the first animal species. Similarly, the mutagenesis procedures provided herein, for example, will enable one to vary the amino acid sequence and N-terminus of lymphotoxin, thereby modifying the pH stability, isoelectric point and the like.

The translated amino acid sequence for human lymphotoxin is described in FIGS. 2a-I/2a-II . Note that this sequence includes a 34 residue presequence which is believed to be removed during normal processing of the translated transcript in human cells (herein, together with its mutants, "pre lymphotoxin"), resulting in the leucyl amino terminal species. The histidyl amino-terminal species is homologous to the leucyl amino-terminal species except that the first 23 amino acids of the leucyl amino-terminal species are absent. All three species, i.e. pre lymphotoxin, leucyl amino-terminal lymphotoxin and histidyl amino-terminal lymphotoxin, as well as their methionyl, modified methionyl, mutant and unglycosylated forms, are included within the scope of lymphotoxin. The unglycosylated leucyl and histidyl amino-terminal species will have lower molecular weights than described above for the homologous species from lymphoblastoid cells.

Pre lymphotoxin is a species of lymphotoxin included within the foregoing definition. It is characterized by the presence of a signal (or leader) polypeptide at the amino terminus of the molecule. Generally, the native signal polypeptide of lymphotoxin is proteolytically cleaved from lymphotoxin as part of the secretory process in which the protein is secreted from the cell. The signal peptide may be microbial or mammalian (including the native, 34 residue presequence), but it preferably is a signal which is homologous to the host cell. Some signal-lymphotoxin fusions are not recognized or "processed" by the host cell into N-terminal met-free lymphotoxin. Such fusions containing microbial signals have utility for example as lymphotoxin immunogens.

Note that the language "capable" of cytotoxic activity means that lymphotoxin includes polypeptides which can be converted, as by enzymatic hydrolysis, from an inactive state analogous to a zymogen to a polypeptide fragment which exhibits the desired biological activity. The language "capable" of in vitro or in vivo cytotoxic activity is intended to embrace noncytotoxic polypeptides which can be converted, as by enzymatic hydrolysis, from an inactive state analogous to a zymogen to a polypeptide fragment which exhibits the definitional biological activity. Typically, inactive precursors will be fusion proteins in which lymphotoxin is linked by a peptide bond at its carboxyl terminus to another protein or polypeptide. The sequence at this peptide bond or nearby is selected, so as to be susceptible to proteolytic hydrolysis to release lymphotoxin, either in vivo or, as part of a manufacturing protocol, in vitro. Typical linking sequences are lys-lys or arg-lys. The nonlymphotoxin component to such a prolymphotoxin is preferably a homologous protein so as to minimize the immunogenicity of the fusion. The homologous protein should be innocuous and not bind to cell surfaces. The lymphotoxin that is so generated then will exhibit the definitionally-required cytotoxic activity.

While lymphotoxin ordinarily means human lymphotoxin, lymphotoxin from sources such as murine, porcine, equine or bovine is included within the definition of lymphotoxin so long as it otherwise meets the standards described above for homologous regions and biological activity. For example, bovine and murine lymphotoxins have been found to be highly (about 80 percent) homologous with human lymphotoxin. Lymphotoxin is not species specific, e.g., human lymphotoxin is active on mouse tumors and neoplastic cell lines. Therefore, lymphotoxin from one species can be used in therapy of another.

Lymphotoxin also includes multimeric forms. Lymphotoxin spontaneously aggregates into multimers, usually dimers or higher multimers. Multimers are cytotoxic and accordingly are suitable for use in in vivo therapy. Lymphotoxin is expressed in recombinant hosts as a monomer. However, lymphotoxin thereafter tends to spontaneously form multimers. Homogeneous multimers or a mixture of different multimers are therapeutically useful.

Variant lymphotoxins include predetermined or targeted, i.e. site specific, mutations of the FIGS. 2a-I/2a-II molecule or its fragments. Variant lymphotoxins are defined as polypeptides otherwise meeting the defined characteristics of lymphotoxin but which are characterized by an amino acid sequence that differs from that of FIGS. 2a-I/2a-II, whether by omission, substitution or insertion of residues. The nonhuman lymphotoxins described herein, and alleles of human lymphotoxin, are to be considered variant lymphotoxins, as are site-directed mutants having no natural counterpart. The objective of mutagenesis is to construct DNA that encodes lymphotoxin as defined above but exhibits characteristics that modify the biological activity of natural lymphotoxin or facilitate the manufacture of lymphotoxin. For example, the lysine +89 codon is mutated in order to express a histidine residue in place of the lysine residue. The histidine +89 is no longer hydrolyzed by trypsin (which generally cleaves proteins at an arg-X or lys-X bond). Protease resistance is expected to confer greater biological half life on the mutant than is the case for lymphotoxin having the sequence of FIGS. 2a-I/2a-II (or a fragment thereof). Other lymphotoxin lysine or arginine residues may be mutated to histidine, for example lysine +28, lysine +19 or arginine +15.

As discussed above, certain regions of the lymphotoxin molecule exhibit substantial homology with a similarly-active protein designated tumor necrosis factor. Amino acid residues in and immediately flanking these substantially homologous regions are preferred for mutagenesis directed to identifying lymphotoxin mutants that exhibit variant biological or cytotoxic activity. Such mutants are made by methods known per se and then screened for the desired biological activity, e.g. increased cytotoxicity towards the particular neoplasm being treated or, in the case of lymphotoxin species intended for immunization of animals, the ability to elicit a more potent immune response. Examples of such lymphotoxin variants are as follows: Ala+168 is mutated to a branched chain amino acid (val, ile, or leu); a hydrophobic amino acid (e.g., phe, val, ile or leu) is inserted between thr+163 and val+164; tyrosine substituted for thr+163; lysine substituted for set+82; isoleucine, leucine, phenylalanine, valine or histidine substituted for ser+42; glutamine, tryptophan, serine or histidine substituted for lys+84; ser+82 deleted; a hydrophobic di-or tripeptide fused to leu+171; aspartic acid or lysine substituted for thr+163; ala-lys inserted between glu+127 and pro+128; lysine or glycine substituted for ser+70; tyrosine substituted for thr+69; arginine or histidine substituted for lys+28; arginine or lysine substituted for his+32; proline, serine, threonine, tyrosine or glutamic acid substituted for asp+36; tyrosine, methionine or glutamic acid substituted for ser+38; threonine, tyrosine, histidine, or lysine substituted for ser+61; aspartic acid, serine or tyrosine substituted for gly+124; arginine, lysine, tyrosine, tryptophan or proline substituted for his+135; aspartic acid substituted for thr+142; and lysine or threonine substituted for gln+146.

A particularly desirable group of mutants are those in which the methionine residues at human lymphotoxin residues +20, +120 and +133 are deleted or, preferably, substituted for by the corresponding residues found in the lymphotoxins of other species such as are described elsewhere herein. For example met+20, +120 and +133 are substituted by threonine, serine and valine, respectively. These are the corresponding residues in bovine lymphotoxin. The substitution is effected in the manner described in Example 9 except that met+133 is mutated to val by a further step of mutagenesis using M13 Mp8 phage in accord with methods known per se. This mutant animal species-hybrid lymphotoxin DNA is used in place of the leucyl amino-terminal DNA of Example 7 and expressed as a fusion. Following known procedures, cyanogen bromide is used to cleave the STII signal from the hybrid lymphotoxin and the mature leucyl amino-terminal lymphotoxin variant recovered.

Other useful variant lymphotoxins are those in which residues from tumor necrosis factor are substituted for corresponding lymphotoxin residues to produce hybrid tumor necrosis factor-lymphotoxin variants. A representative example is the substitution of the first 8, 9 or 10 residues of mature tumor necrosis factor (e.g., val-arg-ser-ser-ser-arg-thr-pro-ser-asp-) for the first 27 residues of leucyl amino-terminal lymphotoxin. This variant is more likely to be N-terminal demethionylated upon direct expression in E. coli.

While the mutation site is predetermined, it is unnecessary that the mutation per se be predetermined. For example, in order to optimize the performance of the mutant histidine +89 lymphotoxin, random mutagenesis is conducted at the codon for lysine +89 and the expressed lymphotoxin mutants screened for the optimal combination of cytotoxic activity and protease resistance.

Lymphotoxin also may contain insertions, usually on the order of about from 1 to 10 amino acid residues, or deletions of about from 1 to 30 residues. Substitutions, deletions, insertions or any subcombination may be combined to arrive at a final construct. Insertions include amino or carboxyl-terminal fusions, e.g. a hydrophobic extension added to the carboxyl terminus. Preferably, however, only substitution mutagenesis is conducted. Obviously, the mutations in the encoding DNA must not place the sequence out of reading frame and preferably will not create complementary regions that could produce secondary mRNA structure. Extracts of *E. coli* transformed with vectors containing DNA encoding lymphotoxin mutants having a deletion of the last 16 carboxy terminal amino acids or deletion of the first about 33 amino terminal residues of leucyl amino-terminal lymphotoxin exhibited no cytotoxic activity. However, the reasons for lack of activity are not known and could have been any of those set forth in Example 1 infra.

Not all mutations in the DNA which encodes the lymphotoxin will be expressed in the ultimated product of recombinant cell culture. For example, a major class of DNA substitution mutations are those DNAs in which a different secretory leader has been substituted for the FIG. 2a-I secretory leader, either by deletions within the 34 residue leader or by substitutions, which exchange of most or all of the native leader for a leader more likely to be recognized by the intended host. For example, in constructing a procaryotic expression vector the FIG. 2a-I secretory leader is deleted in favor of the bacterial alkaline phosphatase or heat stable enterotoxin II leaders, and for yeast the FIG. 2a-I leader is substituted in favor of the yeast invertase, alpha factor or acid phosphatase leaders. This is not to imply, however, that the human secretory leader is not recognized by hosts other than human cell lines. When the secretory leader is "recognized" by the host, the fusion protein consisting of lymphotoxin and the leader ordinarily is cleaved at the leader-lymphotoxin peptide bond in the same event that leads to secretion of the lymphotoxin. Thus, even though a mutant DNA is used to transform the host the resulting product lymphotoxin may be either a fused or native lymphotoxin, depending upon the efficacy of the host cell in processing the fusion.

Another major class of DNA mutants that are not expressed as lymphotoxin variants are nucleotide substitutions made to enhance expression, primarily by avoiding stem-loop structures in the transcribed mRNA (see copending U.S. Ser. No. 303,687, now abandoned, incorporated by reference) or to provide codons that are more readily transcribed by the selected host, e.g. the well-known *E. coli* preference codons for *E. coli* expression.

The mutant nucleic acid is made by known methods per se (A. Hui et al., 1984, "The EMBO Journal" 3(3): 623–629; J. Adelman et al., 1983, "DNA" 2(3): 183–193; U.K. Patent Application 2,130,219A; G. Winter et al., 1982, "Nature" 299: 756–758; and R. Wallace et al., 1981, "Nucleic Acids Research" 9(15): 3647–3656). These methods include M13 phage mutagenesis, synthesis of the mutant lymphotoxin gene as described in Example 1et seq. or other methods as are or will become known in the art.

Nucleic acid encoding lymphotoxin is any DNA or RNA sequence that encodes a polypeptide falling within the definition of lymphotoxin herein, whether or not the nucleotide sequences thereof correspond to the sequences found in nature. In addition, nucleic acid is included within the scope herein that is capable of hybridizing under at least low stringency conditions to nucleic acid encoding lymphotoxin, even if the hybridizing nucleic acid does not encode a protein otherwise meeting the definitional requirements for lymphotoxin. An example of the latter would be a probe that, because of the short length of polypeptide that it encodes, is incapable of expressing a biologically active lymphotoxin. The nucleic acid encoding lymphotoxin or capable of hybridizing therewith is prepared by organic synthesis, substantially as shown in Example 1, or obtained from natural sources by probing genomic or cDNA libraries as shown in the Examples.

The lymphotoxin of this invention is made by a process generally entailing the transformation of a host with a vector bearing the nucleic acid that encodes the desired lymphotoxin. A vector is a replicable DNA construct. Vectors are used herein to amplify DNA or to express DNA which encodes lymphotoxin. An expression vector is a DA construct in which a DNA sequence encoding lymphotoxin is operably linked to a suitable control sequence capable of effecting the expression of lymphotoxin in a suitable host. Such control sequences include a transcriptional promoter, an optional operator sequence to control transcription, a sequence encoding suitable mRNA ribosomal binding sites, and sequences which control termination of transcription and translation.

The vector may be a plasmid, a virus (including phage), or an integratable DNA fragment i.e., integratable into the host genome by recombination). Once transformed into a suitable host, the vector replicates and functions independently of the host genome, or may, in some instances, integrate into the genome itself. In the present specification, "plasmid" and "vector" are sometimes used interchangeably as the plasmid is the most commonly used form of vector at present. However, all other forms of vectors which serve an equivalent function and which are, or become, known in the art are suitable for use herein.

Suitable vectors will contain replicon and control sequences which are derived from species compatible with the intended expression host. Transformed host cells are cells which have been transformed or transfected with lymphotoxin vectors constructed using recombinant DNA techniques. Transformed host cells ordinarily express lymphotoxin. The expressed lymphotoxin will be deposited intracellularly or secreted into either the periplasmic space or the culture supernatant, depending upon the host cell selected.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Suitable host cells are prokaryotes, yeast or higher eukaryotic cells. Prokaryotes include gram negative or gram positive organisms, for example *E. coli* or Bacilli. Higher eukaryotic cells include established cell lines of mammalian origin as described below. A preferred host cell is the phage resistant *E. coli* W3110 (ATCC 27,325) strain described in the Examples although other prokaryotes such as *E. coli* B, *E. coli* X1776 (ATCC 31,537), *E. coli* 294 (ATCC 31,446), pseudomonas species, or Serratia Marcesans are suitable.

Prokaryotic host-vector systems are preferred for the expression of lymphotoxin. A plethora of suitable microbial vectors are available. Generally, a microbial vector will contain an origin of replication recognized by the intended host, a promoter which will function in the host and a phenotypic selection gene, for example a gene encoding proteins conferring antibiotic resistance or supplying an auxotrophic requirement. Similar constructs will be manufactured for other hosts. *E. coli* is typically transformed using pBR322, a plasmid derived from an *E. coli* species (Bolivar, et al., 1977, "Gene" 2: 95). pBR322 contains genes for ampicillin and tetracycline resistance and thus provides easy means for identifying transformed cells.

Expression vectors must contain a promoter which is recognized by the host organism, but cloning vectors need not. The promoter generally is homologous to the intended host. Promoters most commonly used in recombinant DNA construction include the β-lactamase (penicillinase) and lactose promoter systems (Chang et al., 1978, "Nature", 275: 615; and Goeddel et al., 1979, "Nature" 281: 544), a tryptophan (trp) promoter system (Goeddel et al., 1980, "Nucleic Acids Res." 8: 4057 and EPO App. Publ. No. 36,776) and the tac promoter [H. De Boer et al., "Proc. Nat'l. Acad. Sci. U.S.A." 80: 21–25 (1983)]. While these are the most commonly used, other known microbial promoters are Suitable. Details concerning their nucleotide sequences have been published, enabling a skilled worker operably to ligate them to DNA encoding lymphotoxin in plasmid vectors (Siebenlist et al., 1960, "Cell" 20: 269) and the DNA encoding lymphotoxin. At the present time the preferred vector is a pBR322 derivative containing the E. coli, alkaline phosphatase promoter with the trp Shine-Dalgarno sequence. The promoter and Shine-Dalgarno sequence are operably linked to the DNA encoding the lymphotoxin, i.e., they are positioned so as to promote transcription of lymphotoxin mRNA from the DNA.

In addition to prokaryates, eukaryotic microbes such as yeast cultures are transformed with lymphotoxin-encoding vectors. *Saccharomyces cerevisiae*, or common baker's yeast, is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, DNA encoding lymphotoxin (including in particular human pre lymphotoxin), sequences for polyadenylation and transcription termination and a selection gene. A suitable plasmid for lymphotoxin expression in yeast is YRp7, (Stinchcomb et al., 1979, "Nature", 282: 39; Kingsman et al., 1979, "Gene", 7: 141; Tschemper et al., 1980, "Gene", 10: 157). This plasmid already contains the trp1 gene which provides a selection marker for a mutant strain of yeast lacking the ability to grow in tryptophan, for example ATCC No. 44076 or PEP4-1 (Jones, 1977, "Genetics", 85: 12). The presence of the trp1 lesion in the yeast host cell genome then provides an effective environment for detecting transformation by growth in the 25 absence of tryptophan.

Suitable promoting sequences in yeast vectors include the promoters for metallothionein, 3-phosphoglycerate kinase (Hitzeman et al , 1980, "J. Biol Chem.", 255: 2073) or other glycolytic enzymes (Hess et al. 1968, "J. Adv. Enzyme Reg.", 7: 149; and Holland et al., 1978, "Biochemistry", 17: 4900), such as enolase, glyceraldehyde-3-phosphate dehydrogenase, hexokinase, pyruvate decarboxylase, phosphofructokinase, glucose-6-phosphate, isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the lymphotoxin coding sequences to provide polyadenylation of the mRNA and termination.

In addition to microorganisms, cultures of cells derived from multicellular organisms may also be used as hosts. This, however, is not preferred because of the excellent results obtained thus far with lymphotoxin expressing microbes. In principal, any higher eukaryotic cell culture is workable, whether from vertebrate or invertebrate culture. However, interest has been greatest in vertebrate cells, and propagation of vertebrate cells in culture (tissue culture) has become a routine procedure in recent years [Tissue Culture, Academic Press, Kruse and Patterson, editors (11973)]. Examples of useful host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible, and often desirable, to utilize the human genomic promoter, control and/or signal sequences normally associated with lymphotoxin, provided such control sequences are compatible with the host cell systems.

An origin of replication may be provided either by construction of the vector to include an exogenous origin, such as may be derived from SV40 or other viral (e.g. Polyoma, Adenovirus, VSV, or BPV) source, or may be provided by the host cell chromosomal replication mechanism. If the vector is integrated into the host cell chromosome, the latter is often sufficient. Lymphotoxin is prepared without an amino-terminal methionyl by transformation of higher eukaryotic cells with the human pre lymphotoxin DNA.

In selecting a preferred host mammalian cell for transfection by vectors which comprise DNA sequences encoding both lymphotoxin and dihydrofolate reductase (DHFR), it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Natl. Acad. Sci." (USA) 77: 4216.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61).

Transformed host cells are cells which have been transformed or transfected with lymphotoxin vectors constructed using recombinant DNA techniques. Transformed host cells ordinarily express lymphotoxin. The expressed lymphotoxin ordinarily is deposited intracellularly.

Lymphotoxin is recovered from recombinant culture in nonsecreting cells by lysing the cells and removing particulate matter by centrifugation or the like. Lymphotoxin secreting cells are separated from culture supernatant by centrifugation. The contaminated lymphotoxin solution is then purified by the methods referred to above or by immunoaffinity as described in Example 4 below. The lymphotoxin is purified to levels suitable for pharmacological use and placed into conventional dosage forms, e.g. vials or syringes. Mixtures of lymphotoxin variants are employed, e.g. a bank of cytotoxic mutant lymphotoxin species. Lymphotoxin optimally is lyophilized for long term storage, or it may be placed in aqueous solution with stabilizers and excipients, for example isotonic saline, and administered to patients as disclosed by B. Aggarwal et al., European Patent Application 100641.

Lymphotoxin compositions are administered to tumor-bearing animals. The route of administration is in accord with known methods, e.g. intravenous, intraperitoneal, subcutaneous, intramuscular, intralesional infusion or injection of sterile lymphotoxin solutions, or by timed release systems described below. Lymphotoxin is administered intralesionally, i.e., by direct injection into solid tumors. In the case of disseminated tumors such as leukemia, administration is preferably intravenous or into the lymphatic system. Tumors of the abdominal organs such as ovarian cancer are advantageously treated by intraperitoneal infusion using peritoneal dialysis hardware and peritoneum-compatible solutions. Ordinarily, however, lymphotoxin is administered continuously by infusion although bolus injection is acceptable.

Lymphotoxin desirably is administered from an implantable timed-release article. Examples of suitable systems for proteins having the molecular weight of lymphotoxin dimers or trimers include copolymers of L-glutamic acid and gamma ethyl-L-glutamate (U. Sidman et al., 1983, "Biopolymers" 22 (1): 547–556), poly (2-hydroxyethyl-methacrylate) (R. Langer et al., 1981, "J. Biomed. Mater. Res." 15: 167–277 and R. Langer, 1982, "Chem. Tech." 12: 98–105) or ethylene vinyl acetate (R Langer et al.,Id.). Lymphotoxin-containing articles are implanted at surgical sites from which tumors have been excised. Alternatively, lymphotoxin is encapsulated in semipermeable microcapsules or liposomes for injection into the tumor. This mode of administration is particularly useful for surgically inexcisable tumors, e.g. brain tumors.

The amount of lymphotoxin that is administered will depend, for example, upon the route of administration, the tumor in question and the condition of the patient. It will be necessary for the therapist to titer the dosage and modify the route of administration as required to obtain optimal cytotoxic activity towards the target tumor, as can be determined for example by biopsy of the tumor or diagnostic assays for putative cancer markers such as carcinoembryonic antigen, in view of any recombinant toxicity encountered at elevated dosage. Ordinarily, recombinant lymphotoxin dosages in mice at about from 50 to 200 µg/kg body weight/day by intravenous administration have been found to be substantially nontoxic and efficacious in vivo. Obviously, the dosage regimen will vary for different animals.

A method is provided herein for obtaining lymphotoxin-neutralizing antibody. Neutralizing antibody is defined as antibody that is capable of immunologically binding lymphotoxin as defined herein in such a way as to substantially reduce its activity in cytostatic or cytolytic lymphotoxin activity assays such as the murine L929 assay described below. The fact that the antibody is capable of neutralizing lymphotoxin activity does not mean that the antibody must bind directly to the lymphotoxin active or receptor binding site. The antibody may still substantially neutralize lymphotoxin activity if it sterically binds to a region which adjacent to the critical site, i.e., adjacent in the sense of conformationally adjacent and not necessarily adjacent from the point of view of amino acid sequence.

In attempting to prepare a neutralizing monoclonal antibody against lymphotoxin, it proved difficult to immunize mice in a fashion such that lymphotoxin neutralizing antibody is generated or raised in the animals. Neither immunization with lymphoblastoid lymphotoxin nor glutaraldehyde cross-linked lymphotoxin resulted in any detectable neutralizing antibody in the serum of immunized mice, even though the mice did raise non-neutralizing anti-lymphotoxin antibody detectable by enzyme immunoassay. However, immunization with a lymphotoxin-alum (aluminum hydroxide or alumina, $Al_2O_3 \cdot 3H_2O$) adsorption complex will raise neutralizing antibody even in animals which had failed to generate the activity prior to immunization with the alum complex. Preparation of alum and its use in the production of antiserum are disclosed in C. Williams, et al.,eds., 1967, Methods in Immunology and Immunochemistry I, pp 197–229.

Fusions of spleen cells from animals producing neutralizing antibody with murine myeloma cells are made. On the average, about 50 to 100 clones will have to be screened to identify one which synthesizes neutralizing antibody. The process for screening the clones for the desired activity is routine and well within the skill of the ordinary artisan, and can be reproduced with minimal experimental effort.

The serum, plasma or IgG fractions from the immunized animal, as well as immunoglobulins secreted by hybridomas generated from the spleen or lymph cell of immunized animals, are all satisfactory for use herein. In a preferred embodiment the neutralizing antibody is obtained essentially free of other anti-lymphotoxin antibody in hybridoma culture.

The neutralizing antibody is immobilized by adsorption to surfaces, e.g., thermoplastics such as polystyrene, or covalently bound to matrices such as cyanogen bromide-activated Sepharose. It then is used in immunoassays or in immunoaffinity purification. Since the antibody is a neutralizing antibody it is most likely only to adsorb or detect biologically active lymphotoxin or fragments thereof. The antibody is particularly useful in immunoradiometric ("sandwich") immunoassays in concert with a non-neutralizing anti-lymphotoxin monoclonal antibody or a polyclonal antiserum which contains non-neutralizing anti-lymphotoxin. The immunoassay is conducted using either the neutralizing or non-neutralizing antibody as the labelled component, which labelling is effective with a detectable substance such as a fluorescent, chemiluminescent or radio-isotopic label in accord with methods known in the art. For competitive-type lymphotoxin immunoassays, lymphotoxin is labelled in the same fashion. Chloramine-T radioiodination is suitable for both lymphotoxin and lymphotoxin antibody tracer preparation, or the method described in J. Klostergaard et al., "Mol. Immun." 18: 455 (1980) is used.

In order to simplify the Examples certain frequently occurring methods will be referenced by shorthand phrases.

Plasmids are designated by a low case p preceded and/or followed by capital letters and/or numbers. The starting plasmids herein are commercially available, are publically available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 µg of plasmid or DNA fragment is used with about 1 unit of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9:6103–6114, and D. Goeddel et al., 1980, "Nucleic Acids Res." 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98:503–517, and hybridization as described by T. Maniatis et al., 1978, "Cell" 15:687–701.

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53:154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by the method incorporated by reference into Example 1, and then purified on polyacrylamide gels.

All literature citations are expressly incorporated by reference.

EXAMPLE 1

Purification and Sequencing of Lymphotoxin

The human lymphoblastoid cell line RPMI-1788 (ATCC No. CCL-156) was grown in 15 L spinner flasks to a cell density of $4 \times 10^5$ cells per ml using a serum free culture medium (RPMI-1640). Lymphotoxin was induced 10–20 fold (to 500–1000 lymphotoxin units/ml, determined as described below) over basal levels by the inclusion of 20 ng/ml of phorbol myristate acetate in the serum free RPMI-1640 medium. After 65 h of culture, the cells were harvested by filtration, and the lymphotoxin activity in the filtrate was absorbed to controlled pore glass beads (Electronucleonics) in a column (5 cm×20 cm), equilibrated with 5 mM phosphate buffer (pH 7.4) and eluted with 50 percent ethylene glycol in 5 mM phosphate buffer (pH 7.4). 0.1 mM phenylmethyl sulfonyl fluoride (PMSF), a protease inhibitor, and 1 mM sodium azide, for inhibition of microbial growth, were included in all buffers throughout the purification. The eluate from glass beads contained 84,000 units of lymphotoxin/mg protein. This was followed by DEAE cellulose chromatography, Lentil Lectin Sepharose chromatography, and preparative native PAGE as described in B. Aggarwal, et al., 1984, "J. Biol. Chem." 259 (1): 686–691. Homogeneity of the protein responsible for cytotoxic activity was determined by SDS-PAGE, reverse-phase HPLC on a Lichrosorb RP-18 column and by amino terminal sequencing.

This lymphotoxin preparation contained greater than 95 percent by weight of the leucyl amino-terminal lymphotoxin having an approximate molecular weight of 25,000 on SDS-PAGE. The theoretical molecular weight of the protein component of the N-terminal leucyl species is 18,664 daltons; the remaining approximately 6,500 daltons was attributed to a glycosyl side chain at Asn+62, and perhaps other O-linked sugar residues. The tissue culture supernatant contained putative multimers of this species (60,000 Da by TSK-HPLC or 64,000 Da by Sephadex G-100 chromatography).

The remaining 5 percent of the lymphotoxin mixture was the N-terminal histidyl species having a molecular weight of about 20,000. Both species exhibit substantially the same cytolytic activity, at least within the limits of the variation inherent in the murine fibroblast cell lysis assay described below.

Tryptic digestion of the intact lymphotoxin molecules yielded only a few fragments. Histidyl amino-terminal lymphotoxin was digested into two fragments between amino acid positions 89 and 90, while the leucyl amino-terminal tryptic digestion yielded four fragments cleaved between positions 15 and 16, 19 and 20, and 89 and 90.

Micro-sequencing by the Edman degradation technique yielded sequence information on the intact molecule and also on the fragments produced by tryptic cleavage.

Further sequence information was provided by fragments of lymphotoxin produced by carboxypeptidase P and chymotrypsin digestion, acetic acid digestion and cyanogen bromide cleavage. Nearly the entire sequence of the human lymphotoxin was determined by this method. 156 contiguous residues were determined from the amino terminus. It was clear from this sequencing information that the difference between the two lymphotoxin species was the presence of 23 amino-terminal residues in the leucyl amino-terminal species which were not found in the histidyl amino-terminal species. The carboxyl terminal sequence beyond the first three residues proved to be difficult to determine because of certain peptide bonds present in this region and the hydrophobic nature of the residues.

A synthetic gene was designed which would code for the protein sequence to the extent determined by micro-sequencing. The gene design incorporated a general *E. coli* codon bias, that is, rarely used *E. coli* codons were not used in the sequence. Human preference codons were substituted where no *E. coli* codon bias was apparent. This bias was chosen to aid in expression in *E. coli*, and also so that the synthetic gene would be useful as a probe to identify the natural DNA sequence from human cDNA or genomic libraries. The unique restriction sites XbaI, BamHI, HindIII, and BglII were designed into the sequence to aid in the construction of the fragments and to allow for future manipulation of the gene.

The 58 original oligomers designed for the synthetic lymphotoxin gene were synthesized by the solid phase phosphite method of M. Matteucci et al., 1981, "J. Amer. Chem. Soc." 103: 3185-3190 and S. Beaucage et al., 1981, "Tet. Letters" 22: 1859-1862. The size of these oligomers ranged from 16 bases to 20 bases and is shown in FIG. 1a. Overlaps between oligomers were 6 bases in length and designed to be unique. The entire gene was assembled as shown in FIGS. 1b-I and 1b-II.

The gene was constructed in three separate pieces. The first, Segment A, was 117 base pairs in length and represented the 5' coding region for the amino terminal end of the leucyl amino-terminal species. Segment B represented the DNA encoding the middle of the lymphotoxin molecule and was 145 base pairs in length. Segment C, at 217 base pairs in length, was believed to encode all but 16 amino acid residues at the lymphotoxin carboxy terminus. The oligomers required to synthesize each of the segments were purified by electrophoresis and then pooled. The relatively small size of each oligomer (that is, 16 to 20 bases) was chosen to reduce errors in synthesis.

Each group of oligomers was phosphorylated in a reaction containing 20 mM Tris-HCl (pH 7.5), 10 mM $MgCl_2$, 20 mM dithiothreitol, 0.5 mM ATP, and 15 units of T4 polynucleotide kinase in a volume of 50 µl; approximately 50 pmol of each oligomer was contained in the reaction. After 30 minutes at 37° C., the reaction was heated to 65° C. to destroy kinase activity, and then allowed to slowly cool to 20° C. over the period of one hour. The phosphorylated oligomers were then ligated by the addition of 10 units of T4 DNA ligase and the reaction was allowed to proceed for 2 hours at 20° C. The DNA ligase was heat inactivated and then the ligated oligomers were digested for 3 hours at 37° C. with restriction endonucleases which recognized the designed terminal sites (e.g., XbaI and BamHI for segment A). Fragments for each segment were isolated by electrophoresis on a 7 percent polyacrylamide gel. Fragments of the correct mobility were identified for each segment by ethidium bromide staining and electroeluted from the gel. pFIFtrp69 (D. Goeddel et al., 1980, "Nature" 287: 411-416 or Crea et al., European Patent Application 0048970) was digested with XbaI and BamHI and the large vector fragment isolated by 6 percent polyacrylamide gel electrophoresis. About 50 ng of segment A was ligated to the pFIFtrp69 fragment. Similarly, segment B was ligated into BamHI and HindIII digested pBR322, and segment C was ligated into HindIII and BglII digested pLeIFA-125-1 (D. Goeddel et al., 1980, "Nuc. Acids Res." 8: 4057-4073). The ligation reaction mixtures were transformed into *E. coli* ATCC 31446 and the resulting recombinant plasmids were characterized by restriction endonuclease analysis and DNA sequencing by the Maxam and Gilbert chemical degradation method. Five of six segment A clones contained the designed sequence. Four segment B and four segment C plasmids were isolated, and all of these inserts had the correct sequences. Each segment was isolated by digestion with restriction endonucleases which recognized the terminal sites and then ligated into the plasmid vector pFIFtrp69 digested with XbaI and BglII. The resulting recombinant plasmid, pLTXB1, was characterized by sequencing the inserted XbaI-BglII fragment, which contained the sequence presented in FIG. 1a.

To determine if the synthetic gene would indeed produce biologically active lymphotoxin, the *E. coli* pLTXB1 transformants were grown in minimal media under conditions to de-repress the trp promoter and allow expression of the synthetic lymphotoxin gene. Cultures were grown to an optical density of 1.0 at 550 nanometers and harvested by centrifugation. The cell pellet was suspended in one-tenth volume, and then lysed by sonication.

Lymphotoxin activity was determined by the modified cell-lyric assay of B. Spofford, 1974, "J. Immunol." 112: 2111. Briefly, mouse L-929 fibroblast cells were grown in microtiter plates in the presence of actinomycin D. After 12-18 hours, 0.125 ml of serially diluted sample to be assayed for lymphotoxin is added to each well. After 18 hours, the plates were washed and the lysis of the cells induced by lymphotoxin was detected as adhering to the plates by staining the plates with a 1 percent solution of crystal violet in methanol:water (1:4 v/v). The intensity of stain was observed both visually as well as spectrophotometrically at absorbance of 450 nm and 570 nm transmission using a Dynatech spectrophotometer. The cells Plated in a microtiter well with culture medium alone were set at 0 percent lysis whereas those with 3M guanidine hydrochloride solution provided an end point for 100 percent lysis. One unit of lymphotoxin is defined as the amount required for 50 percent cell lysis out of 12,000 cells plated in each well. Note that other assays of cytotoxic activity also may be used. For example see B. Aggarwal et al., in "Thymic Hormones and Lymphokines", 1983, ed. A. Goldstein, Spring Symposium on Health Sciences, George Washington Univ. Medical Center (the A549 cell line referred to in this material is available from the ATCC as CCL185). Culture lysates showed undetectable cytolytic activity in the murine cell assay described above. Control lysates from gamma interferon expressing cultures did contain gamma interferon activity. This result suggested that the synthetic gene did not encode an active lymphotoxin. There were several possible explanations for this. For example: (1) the E. coli degraded the lymphotoxin, (2) the lymphotoxin gene was not transcribed in E. coli, (3) the lymphotoxin message was not translated in E. coli, (4) the protein did not have the proper sequence due to a protein sequencing error, or (5) the 16 residue carboxy terminal sequence or a portion thereof was actually necessary for activity or for proper configuration of the lymphotoxin molecule.

EXAMPLE 2

Procedure for Obtaining cDNA Encoding Lymphotoxin

RNA was isolated from a culture of a non-adherent cell fraction of human peripheral blood lymphocytes 48 hours after induction with phorbol myristate acetate (10 ng/ml), staphylococcal enterotoxin B (1 μg/ml) and thymosin α-1 (S. Berger et al., 1979, "Biochemistry" 18: 5143–5149). This culture was producing 400 units of lymphotoxin activity/ml of supernatant. The mRNA was concentrated by adsorption to immobilized oligo dT, eluted and cDNA prepared by reverse transcription (P. Gray et al., 1982, "Nature" 295: 503–508). Reverse transcriptase was used to make a cDNA copy of the messenger RNA by standard methods, a second strand was prepared (also by standard methods) by Klenow treatment, and the cDNA was treated with S-1 nuclease to remove the hairpin loop. In order to insert this cDNA into a vector the ends were ligated to an adaptor or linker so as to create 5' and 3' restriction enzyme sites or, preferably, cohesive terminii for a predetermined restriction enzyme site. The oligonucleotide 5' HO-AATTCATGCGTTCTTACAGGTACGCAAGAATGTC-P 5' was used for this purpose. The oligonucleotide was ligated to the cDNA and the cDNA reisolated by polyacrylamide gel electrophoresis. λgt10, a publicly available phage (or its substantial equivalent, λgt11, which is available from the ATCC), was digested with EcoRI and the linear fragment recovered (M. Wickens et al., 1978, "J. Biol. Chem." 253: 2483–2495). The linkered reverse transcript and the λgt10 digest were ligated and the ligation mixture used to transfect E. coli C-600 or other known host susceptible to λ phage infection. Approximately 10,000 recombinant phage were plated on a 15 cm plate and screened by a low-stringency plaque hybridization method (T. Maniatis et al., 1978, "Cell" 15: 687–701 and P. Gray et al., ¡PNAS" 80: 5842–5846) using a $^{32}$P-labelled probe prepared from Segment A of FIG. 1a by the method of J. Taylor et al., 1976, "Biochem. Biophys. Acta" 442: 324–330 in which calf thymus DNA primers were used (PL Biochemicals). Duplicate nitrocellulose filters were hybridized by the low stringency method with 5×10$^7$ cpm of the probe in 20 percent formamide. The filters were washed twice in 0.3M sodium chloride, 0.03M sodium citrate, and 0.1 percent sodium dodecyl sulfonate (SDS) at 37° C.

Two phages hybridized with the probe and were plaque purified. The purified phages hybridized with both the Segment A probe and a probe prepared from Segment B. The cDNA inserts of the two hybridizing phages, λLT1 and λLT2, were subcloned into M13mp8 and sequenced by the dideoxy chain termination method (A. Smith, 1980, "Methods in Enzymology" 65: 560–580). The insert in λLT2 was only about 600bp and did not contain the entire 3' coding region for lymphotoxin. The insert in λLT1 contained the entire coding region for leucyl amino-terminal lymphotoxin plus a 650 bp 3' untranslated region (containing a consensus polyadenylation signal) and codons for 18 amino acids amino terminal to the leucyl terminus. Since this did not constitute the entire lymphotoxin coding region an additional $^{32}$P-labelled probe was prepared from the cDNA insert of λLT1 and used to screen an additional 25,000 recombinant λgt10 phages at high stringency (see T. Huynh et al., 1984, in *Practical Approaches in Biochemistry* IRL Press, Oxford). Twelve additional hybridizing phages were isolated and the sequence of the longest insert, from λLT11, is presented in FIGS. 2a-I/2a-II. The longest open reading frame was translated starting at the first observed ATG. Numbers above each line refer to amino acid position and numbers below each line refer to nucleotide position. The leucyl residue labelled "1" represents the first residue sequenced of leucyl amino-terminal lymphotoxin (FIG. 1a) and is presumably the first amino terminal residue of the mature species of lymphotoxin. The first 34 residues represent a signal sequence. Residues 156–171 had not been determinable by protein sequencing of lymphotoxin, but instead were imputed from the nucleotide sequence.

EXAMPLE 3

Figure 2B:
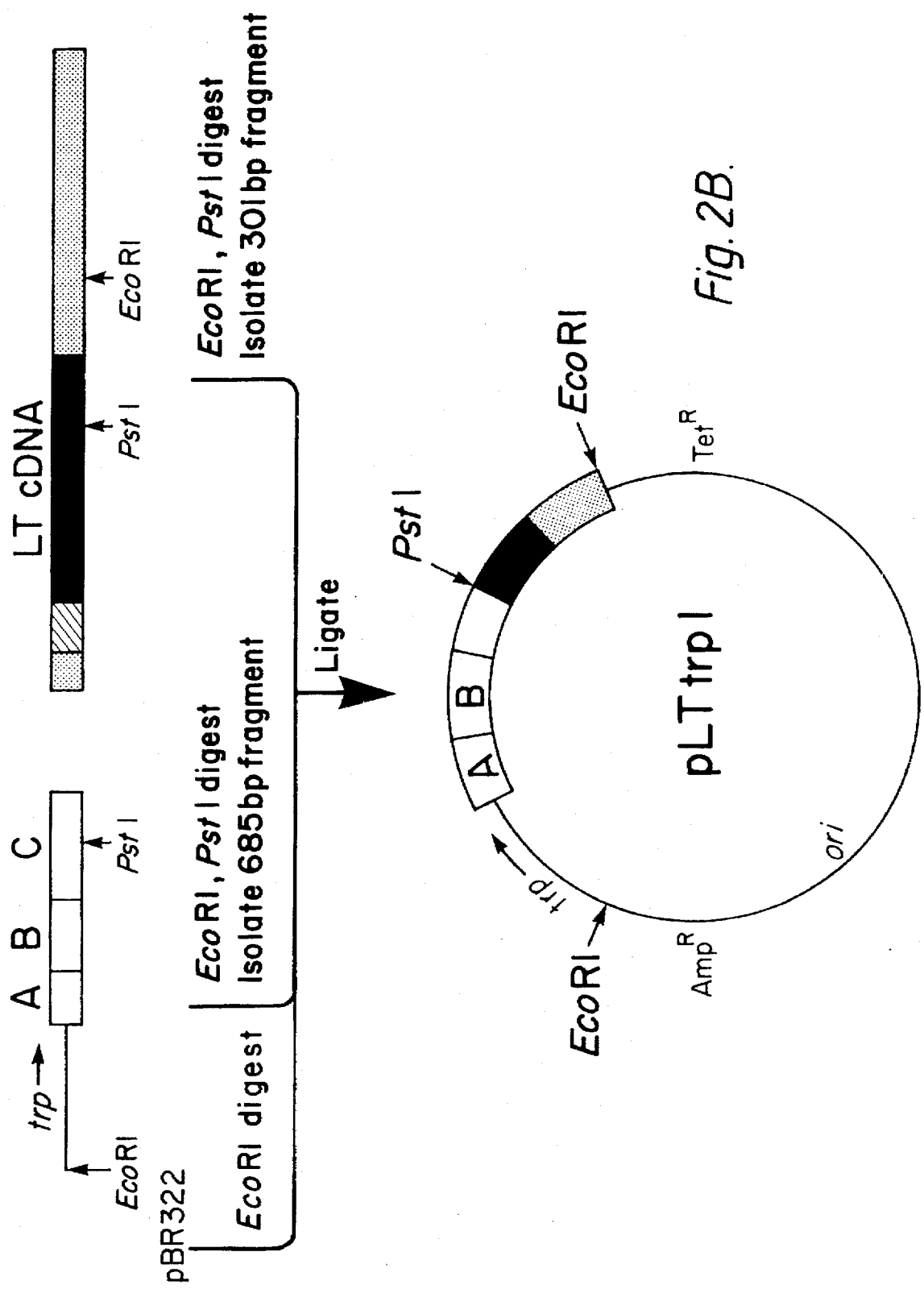

Construction of a Hybrid Synthetic Gene/Natural cDNA Expression Vector for Leucyl Amino-Terminal Lymphotoxin This construction is shown in FIG. 2b. pLTXB1 (containing the inactive synthetic gene) was partially digested with EcoRI and PstI, and a 685 bp fragment containing DNA encoding 125 N-terminal residues of lymphotoxin was recovered. A partial PstI digest was performed because of the presence of an additional PstI site at residue 10 (FIG. 1a). A 301 bp fragment containing DNA encoding the C-terminal 51 amino acids of lymphotoxin was isolated by digesting the subcloned cDNA of λLT1 with EcoRI and PstI (these sites are shown above in FIG. 2a at nucleotide positions 554 and 855). These fragments were isolated by electrophoresis on 5 percent polyacrylamide and electroelution. The fragments were ligated into pBR322 which had been digested with EcoRI and dephosphorylated with bacterial alkaline phosphatase to reduce background transformants. The resulting expression plasmid, pLTtrp1, was characterized as to proper orientation and sequence by restriction endonuclease digestion and DNA sequencing. Leucyl amino-terminal lymphotoxin was expressed by transforming E. coli 31446 with pLTtrp1 and culturing the transformants in medium containing tetracycline at 37° C. for 4–6 hours until an OD. of 1.0 was reached. The cell lysates contained cytotoxic activity. The leucyl amino terminus of the expressed lymphotoxin species was found to be substituted with a blocked methionyl residue. It is believed that the product of this synthesis is the formyl methionyl rather than methionyl species.

EXAMPLE 4

Immunoaffinity Purification of Lymphotoxin

A murine monoclonal cell line secreting anti-lymphotoxin (Example 8) was grown in mice and purified from ascites fluid by ion exchange chromatography. The anion exchange eluate was coupled to cyanogen bromide activated Sepharose at a concentration of 2 mg/ml resin. A 20 ml column was equilibrated consecutively with TBS (containing 0.05M Tris-HCl , pH 7.0, 0.15M sodium chloride, and 2 mM EDTA); then with elution buffer (containing 0.1M acetic acid, pH 4.5, 150 mM sodium chloride); and finally with TBS. A 40 percent saturated ammonium sulfate precipitate of pLTtrp1-transformed *E. coli* sonicated lysate (previously clarified by centrifugation) was suspended in 0.1M Tris-HCl, pH 7.4, and 5 mM EDTA and loaded onto the column at a rate of one column volume per hour. Following extensive washing with TBS containing 0.05 percent Tween-20, specifically bound material was eluted with the elution buffer, the pH immediately adjusted to 7.8 with 0.1 volume 1M Tris-HCl, pH 8.5, and stored at 4° C. The specific activity of this purified lymphotoxin was 2–10×10$^7$ units/mg, as measured in the above murine L-929 assay.

The eluate contained most of the activity loaded onto the column. The majority of the total eluate protein migrated as a single band under both reducing and nonreducing conditions in SDS-polyacrylamide gel electrophoresis. The mobility of this band corresponds to approximately 18,000 NW, which is consistent with the predicted value of 18,664 MW fur unglycosylated leucyl-amino terminal lymphotoxin based on the deduced amino acid sequence. To further characterize its biological activities, the purified recombinant lymphotoxin was tested for cytolytic activity in vitro and antitumor activity in vivo.

EXAMPLE 5

In Vivo Biological Activity of Recombinant Lymphotoxin

Recombinant and lymphoblastoid lymphotoxin were tested in an in vivo tumor necrosis assay. MethA(a) sarcomas were grown for 7–10 days in susceptible mice [BALB/C×C57B1/6fl or CB6fl], and the tumors then directly injected with Example 4 lymphotoxin, lymphoblastoid lymphotoxin (prepared and purified as described above) or control samples. After 20–24 hours, the mice were sacrificed, the tumors removed and histologically scored for the extent of necrosis. As shown in Table 1, both recombinant and lymphoblastoid lymphotoxin caused significant necrosis of MethA(a) sarcoma in vivo. Control samples did not induce necrosis of the MethA(a) sarcomas.

TABLE 1

NECROSIS OF MethA(a) SARCOMA IN VIVO BY RECOMBINANT AND NATURAL LYMPHOTOXIN

| Treatment | Number of Mice Sarcoma Necrosis Score | | | |
|---|---|---|---|---|
| | +++ | ++ | + | − |
| Buffer 1 control | — | — | — | 3 |
| Lymphoblastoid Lymphotoxin, 25,000 units | 4 | — | — | — |
| Lymphoblastoid Lymphotoxin, 10,000 units | 4 | — | — | — |
| Recombinant Lymphotoxin, 200,000 units | 14 | 2 | 2 | — |
| Recombinant Lymphotoxin, 25,000 units | 3 | — | — | 1 |
| Recombinant Lymphotoxin, 10,000 units | 3 | — | 1 | — |
| Buffer 2 Control | — | — | — | 9 |

Lymphoblastoid lymphotoxin was injected dissolved in buffer 1 (0.01M Tris-HCl, 0.05M (NH$_4$)$_2$HCO$_3$, pH 8.0) and recombinant lymphotoxin was injected dissolved in Buffer 2 (0.15M NaCl, 0.1M sodium acetate and 0.1M Tris-HCl, pH 7.8).

The absence of carbohydrate on recombinant lymphotoxin does not appear to affect biological activity, since the specific activity of lymphotoxin produced by recombinant culture (2–10×10$^7$ units/mg) is approximately the same as that reported for lymphoblastoid lymphotoxin (4×10$^7$ units/mg).

The recombinant lymphotoxin activity also exhibited thermolability similar to natural lymphotoxin, i.e., inactivation in aqueous solution after heating for 1 hour at 80° C.

EXAMPLE 6

Figure 3A:
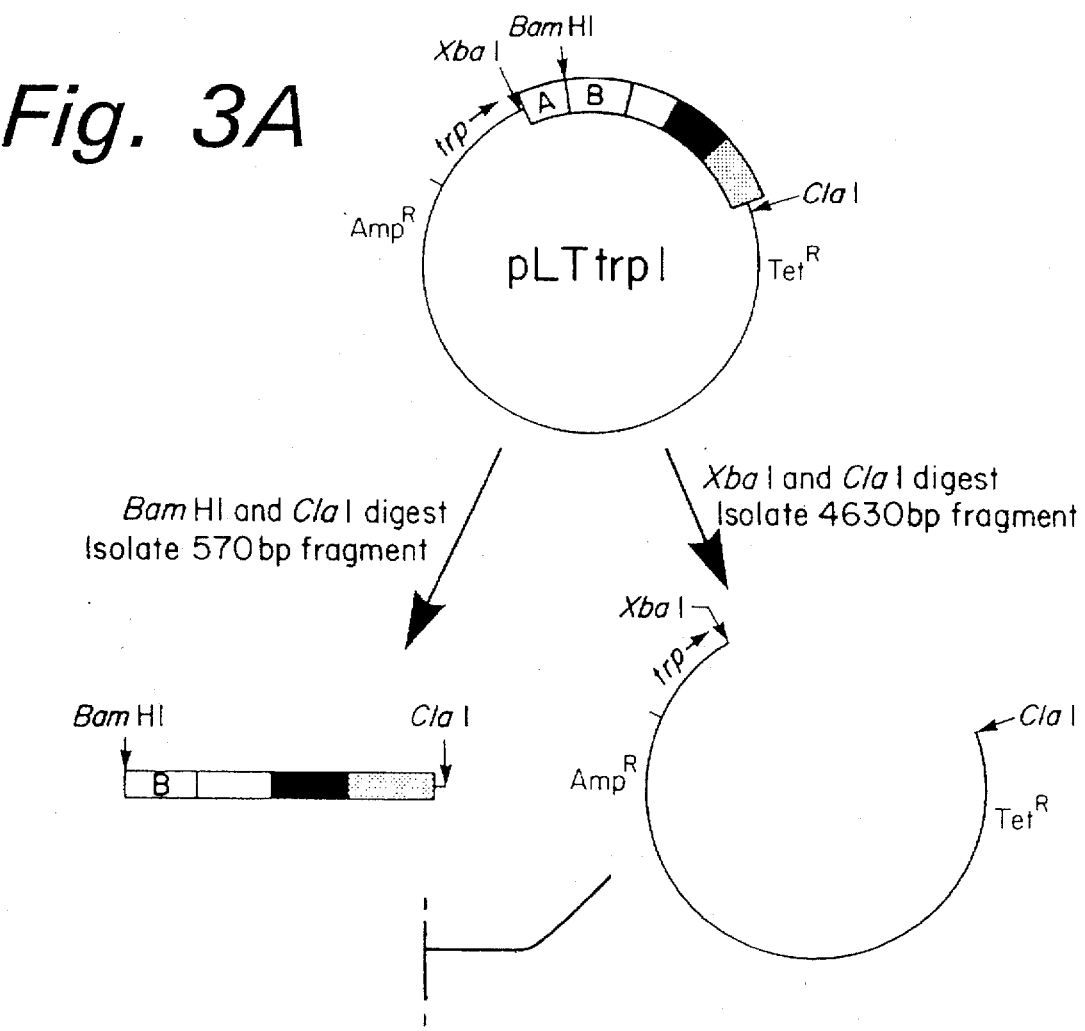
FIGS. 3-I and 3-II show a method of constructing an expression vector for methionyl histidyl amino-terminal lymphotoxin.
Figure 3B:
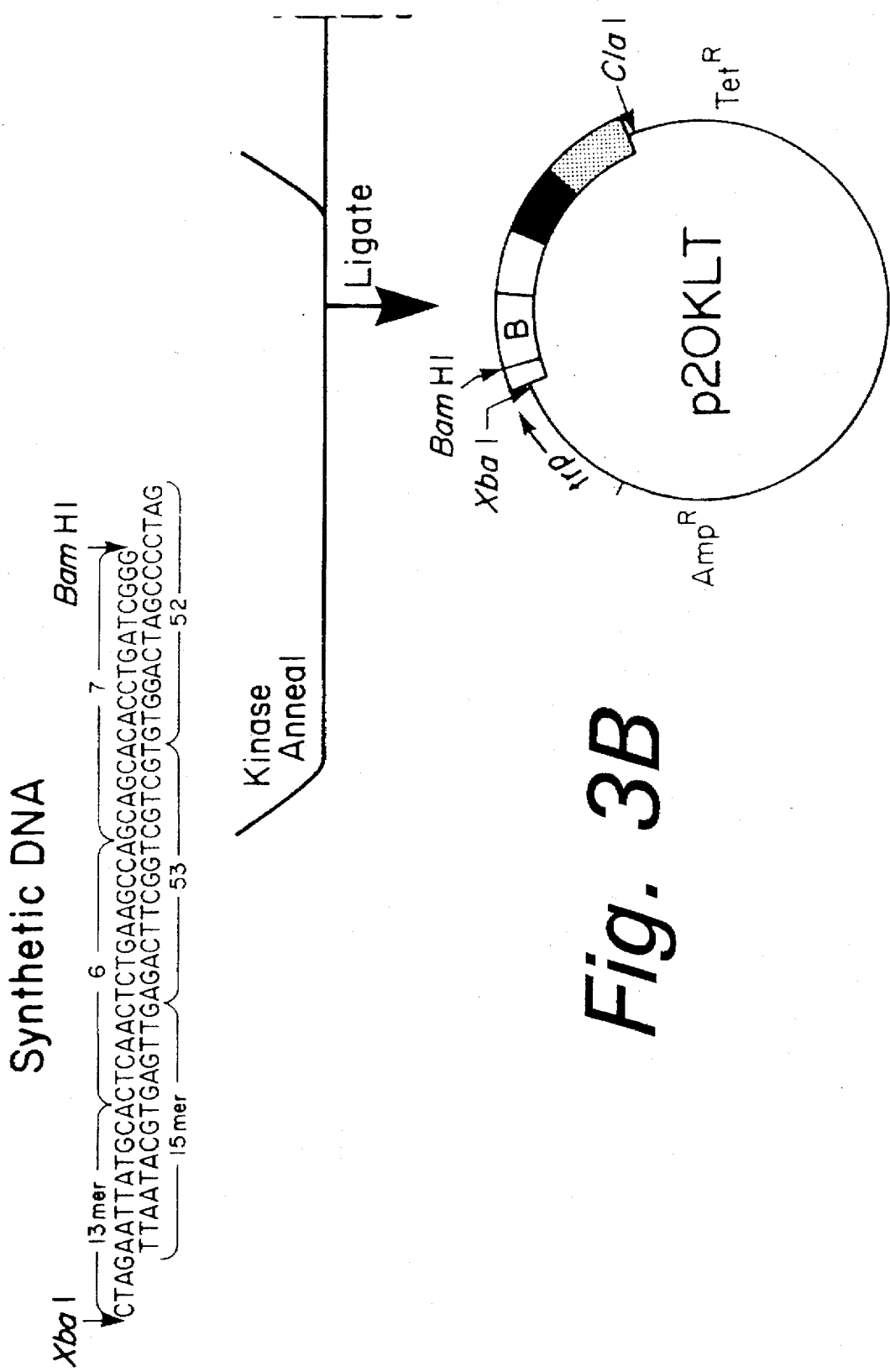
Figures 1, 5A:
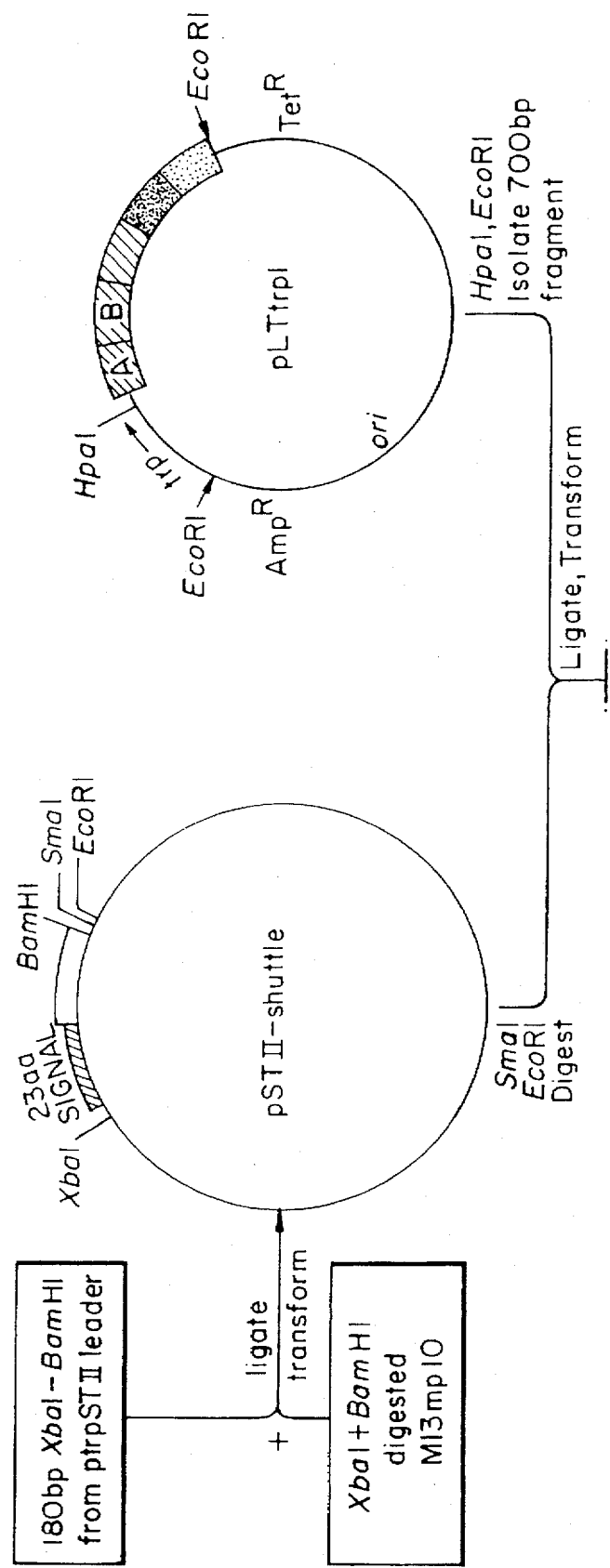
Figures 2, 5A:
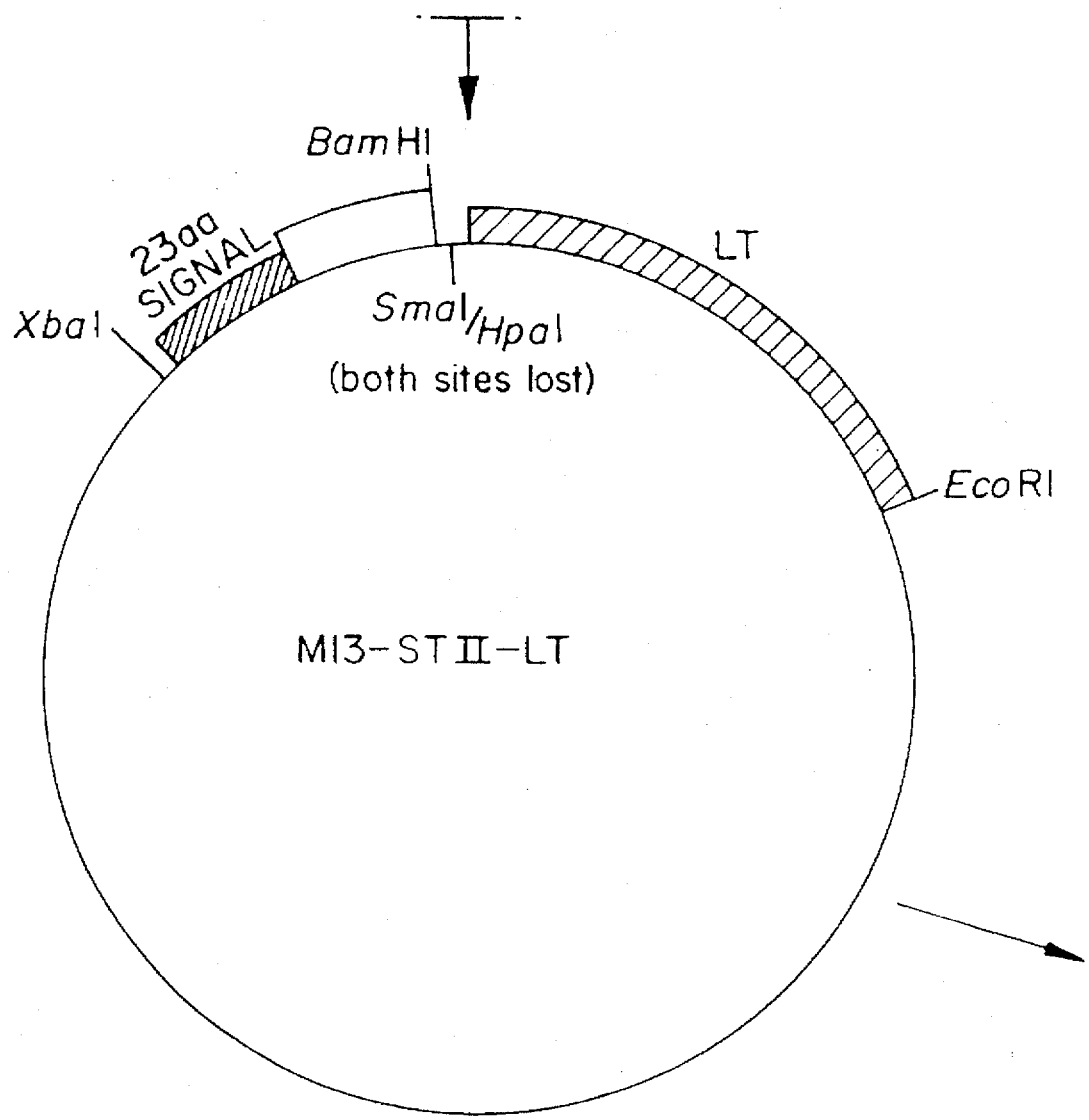
Figures 1, 5B:
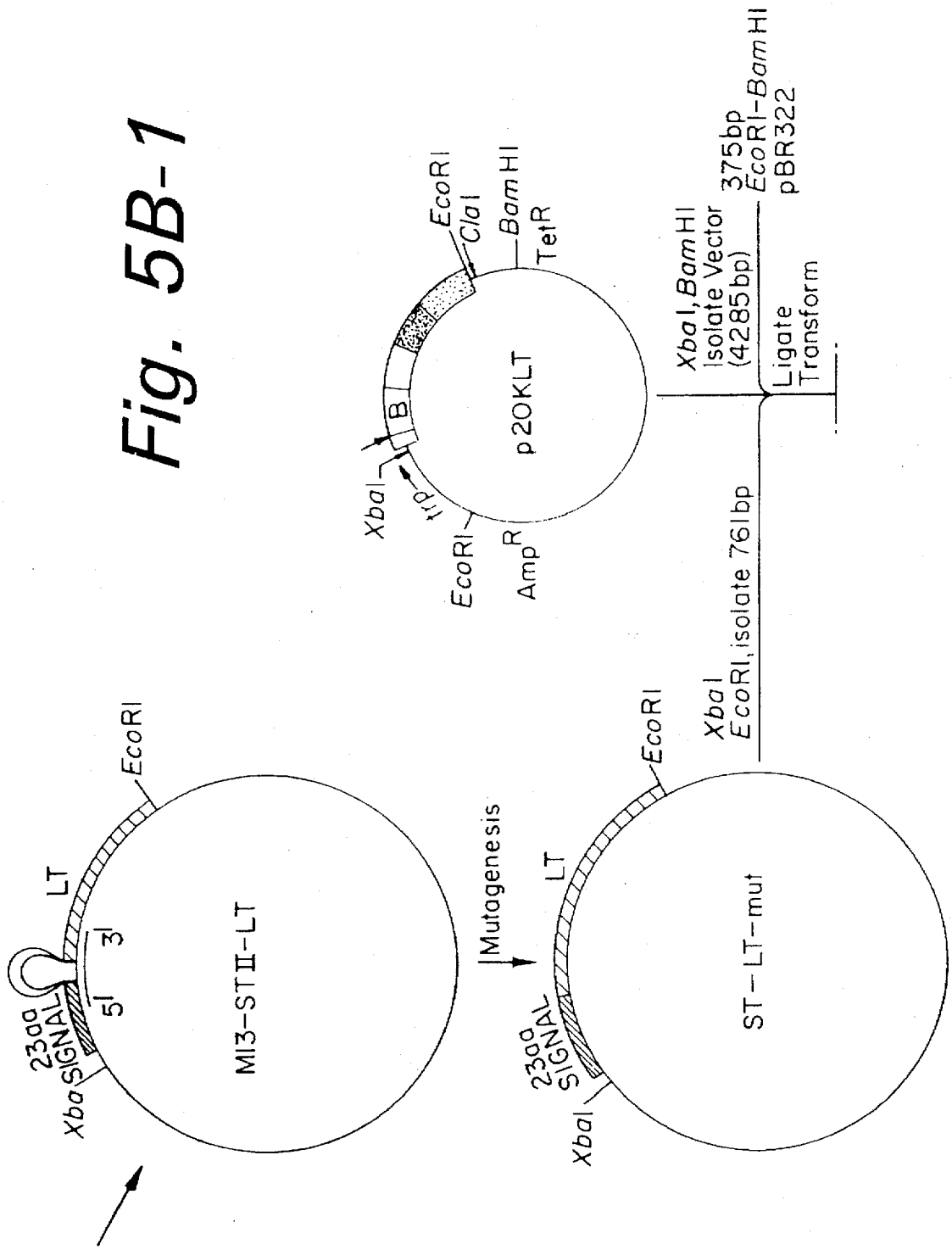
Figures 2, 5B:
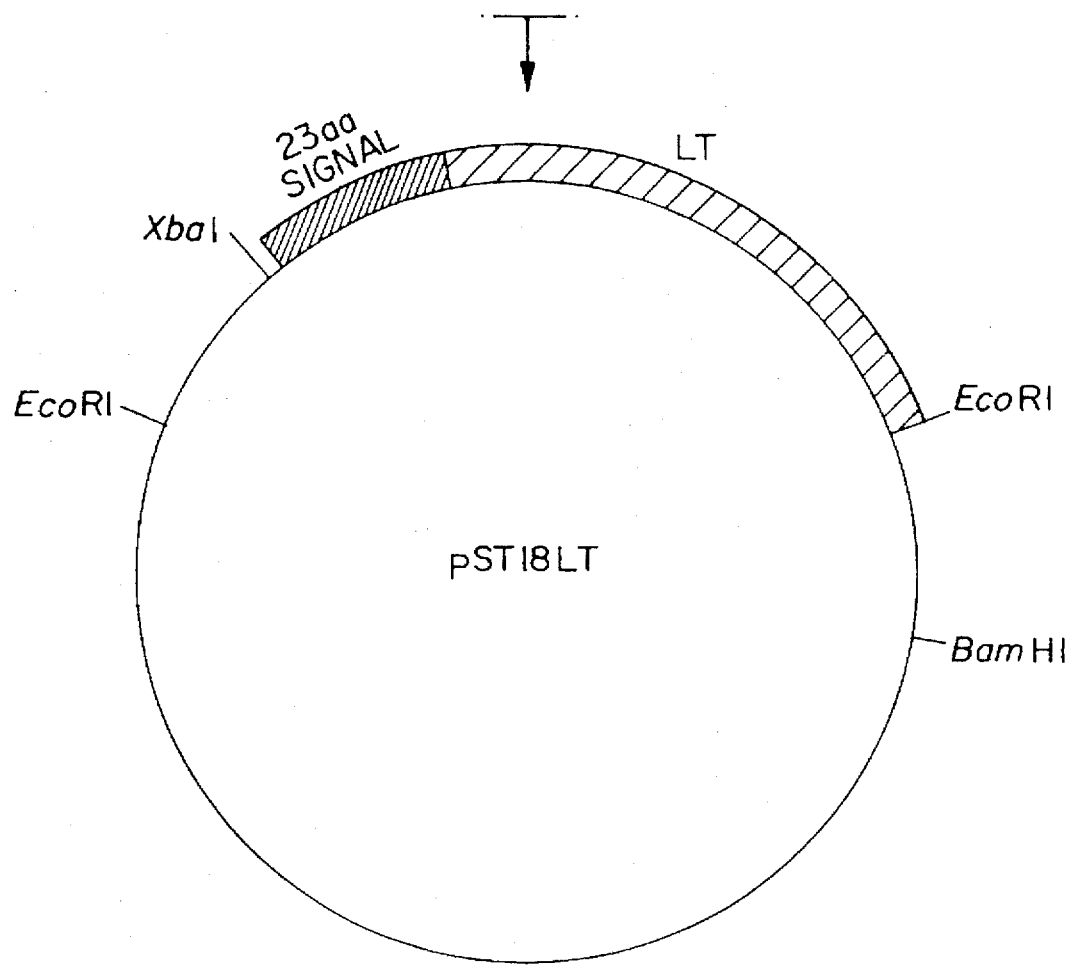

Construction of an Expression Vector for Methionyl Histidyl Amino-Terminal Lymphotoxin Construction of a plasmid which directs the expression in *E. coli* of methionyl histidyl amino-terminal lymphotoxin is outlined in FIGS. 3-I and 3-II. A synthetic oligonucleotide was inserted into the expression plasmid so as to encode an initiator methionine codon adjacent to the histidyl codon of histidyl amino terminal lymphotoxin (residue 24 of FIG. 2a-I). This was performed by isolating a 4630 bp vector fragment from pLTtrp1 by XbaI and ClaI digestion, preparative 1 percent agarose gel electrophoresis, and electroelution. A 570 bp BamHI-ClaI fragment containing most of the lymphotoxin coding sequence was also isolated from pLT-trp1 in the same fashion. To synthetic oligonucleotides were synthesized by methods discussed previously and mixed with oligonucleotides 6, 7, 52 and 53 of FIG. 1a. Approximately 50 pmol of each oligonucleotide was treated with polynucleotide kinase as described in Example 1. The oligonucleotides were annealed and then ligated with a mixture of the 570 bp BamHI-ClaI fragment and the 4630 bp XbaI-ClaI vector fragment. The ligation mixture was transformed into *E. coli* ATCC 31446 and recombinants were selected on the basis of resistance to tetracycline. Plasmid p20KLT was recovered from one of the transformants. Plasmid p20KLT was characterized by restriction enzyme and DNA sequence analysis.

EXAMPLE 7

Preparation of Cytotoxic Lymphotoxin Fusion Variant

A plasmid containing DNA encoding a fusion of lymphotoxin with a bacterial protein was constructed by cloning a sequence coding for a bacterial signal sequence adjacent to the structural gene for lymphotoxin. The sequence of the gene for the heat-stable Enterotoxin II (STII) of *E. coli* has been characterized (R. N. Picken et al., 1983, "Infection and Immunity" 42: 269–275) and encodes a 23 amino acid signal sequence which directs the secretion of the STII into the periplasmic space of *E. coli*

The plasmid pWM501 (Picken et al., 1983, "Infection and Immunity" 42[1]: 269–275) contains the heat-stable enterotoxin (STII) gene. A portion of the DNA which encodes the STII gene was recovered from pWM501 using the following steps. pWM501 was digested with RsaI and the 550 bp DNA fragment was isolated. This gene fragment was ligated to the phages M13mp8 (J. Messing et al. in the *Third Cleveland Symposium on Macromolecules: Recombinant DNA*, Ed. A. Walton, Elsevier, Amsterdam [1981] pp 143–153) that had been previously digested with SmaI. The ligated DNA was used to transform *E. coli* JM101, a commercially available strain for use with the M13 phages. Clear plaques were recovered. The double stranded M13mp8 STII Rsa derivative was isolated from an *E. coli* JM101 infected with this phages using standard procedures (J. Messing et al. op cit). By the use of the M13mp8 subcloning procedure just described the approximately 550 base pair fragment containing the STII leader gene is now bounded by a series of different restriction endonuclease sites provided by the phages. The M13mp8 STII Rsa derivative then was digested with EcoRI and Pst I and a DNA fragment slightly larger than the 550 bp DNA fragment was isolated.

The EcoRI-PstI fragment was subcloned into pBR322. This was accomplished by digesting pBR322 with EcoRI and PstI and isolating the vector. The isolated vector was ligated to the EcoRI-PstI DNA fragment. This DNA mixture was used to transform *E. coli* ATCC 31446 and tetracycline resistant colonies selected. A plasmid was isolated from a resistant *E. coli* colony and designated pSTII-partial.

pSTII-partial was digested with MnlI and BamHI and a 180 bp fragment containing the STII Shine-Dalgarno sequence, the STII signal sequence, and the first 30 codons of the mature STII gene was isolated. The 180 bp DNA fragment was ligated to a plasmid containing the trp promoter. One such plasmid, pHGH207-1, has been described previously (H. de Boer et al., 1982, in: *Promoters: Structure and Function*, Eds. R. Rodreguez et al. Chamberlin, Praeger Pub., New York, N.Y., pp 462–481). A derivative of this plasmid, pHGH207-1*, wherein the EcoRI site 5' to the trp promoter had been converted to EcoRI* by filling in with DNA polymerase I (DNA pol I) and joining the blunt ends by ligation (S. Cabilly et al., 1984, "Proc. Natl. Acad. Sci. USA" 81: 3273–3277) was used in this example. The trp promoter-containing plasmid was digested with XbaI and treated with DNA pol I and all four dNTPs to fill in the protruding sequence. The DNA preparation was then digested with BamHI and the vector-containing fragment isolated. This vector fragment then was ligated to the 180 bp STII signal-containing DNA fragment isolated above. The ligation mixture was used to transform *E. coli* ATCC 31446 to ampicillin resistance. A plasmid designated STII-leader was isolated from an ampicillin resistant colony.

An M13 phage containing STII encoding sequences was first constructed by ligating the 180 bp XbaI-BamHI fragment of pSTII-leader into XbaI and BamHI digested M13mp10. The resulting phage DNA, pSTII-shuttle, was characterized by restriction endonuclease analysis and nucleotide sequencing. LT encoding sequences were then introduced into this vector by ligating the HpaI-EcoRI 700 bp fragment of pLTtrp1 into SmaI-EcoRI digested pSTII-shuttle replicative form (RF, double stranded) DNA; SmaI and HpaI sites are both blunt ended and ligated together (resulting in the loss of both sites). The resulting phages DNA, M13-STII-LT, was characterized and then utilized for mutagenesis as follows: the primer 5' p CAAATGCCTAT-GCACTGCCAGGCGTAGG was kinased and mixed with the template (M13-STII-LT) in the presence of ligase buffer and XbaI-EcoRI digested M13mp10 RF DNA (to promote priming of DNA, as reported by J. P. Adelman et al., 1983, "DNA" 2: 183—193); the mixture was heated to 95° C. and then allowed to anneal at room temperature for 30 minutes and then placed on ice for 30 minutes. All four deoxynucleotide triphosphates were then added along with ATP, T4 DNA Ligase, and the large fragment (Klenow) of *E. coli* DNA polymerase I. The mixture was incubated 1 hour at 14° C. and then used to transfect competent *E. coli* JM101, a commercially available strain, or any other M13 phages host. Correctly mutagenized phage were identified by hybridization screening utilizing the $^{32}$P-radiolabeled-primer as a probe. The resulting phages ST-LT-mut was characterized by DNA sequence analysis. Replicative form DNA was prepared from this phage and used for isolation of a 761 bp XbaI-EcoRI fragment containing DNA for the STII signal sequence adjacent to the coding sequence of Leucyl-amino terminal lymphotoxin. This DNA was ligated with XbaI-BamHI digested p20KLT (the large 4285 bp vector fragment) and the 375 bp EcoRI-BamHI fragment of pBR322. The resulting plasmid, pST18LT, was characterized by restriction mapping and DNA sequencing. A similar construction was prepared that encoded a fusion of the STII signal amino-terminal to the histidine residue of histidyl amino-terminal lymphotoxin. The resulting plasmids were transformed into *E. coli* ATCC 31446. Plasmids pSTLT18 and pSTLT16 were recovered. They were confirmed to encode the STII fusion by restriction enzyme analysis and dideoxy sequencing. *E. coli* transformed with plasmids pSTLT18 or pSTLT16 synthesize STII signal sequence fusions with leucyl amino-terminal and histidyl amino-terminal lymphotoxin as determined to be consistent with the calculated molecular weights by gel electrophoresis. The *E. coli* lysates containing these fusion proteins exhibited cytotoxic activity.

EXAMPLE 8

Method for Making Monoclonal Murine Antibody Capable of Neutralizing Lymphotoxin Purified lymphoblastoid lymphotoxin obtained in Example 1 was dialyzed against phosphate buffered saline (PBS). 200 μg of lymphotoxin/ml were contained in the dialysate. Glutaraldehyde was added to the dialysate to a concentration of 70 mM glutaraldehyde, the mixture incubated for 2 hours at room temperature, more glutaraldehyde added to bring its total added concentration up to 140 mM, incubation continued for another 6 hours and the mixture then dialyzed against PBS. 50 μg of the glutaraldehyde cross-linked lymphotoxin (hereafter, "polylymphotoxin") and 0.5 ml of Freund's complete adjuvant was injected subcutaneously into mice (strain BALB/c). After one week, the mouse was booster immunized with 50 μg of polylymphotoxin and 0.5 ml of Freund's incomplete adjuvant, half intramuscularly and half into the peritoneal cavity. Serum was harvested after 7 days and assayed for anti-lymphotoxin activity by an ELISA assay.

The ELISA assay was conducted as follows: A buffered solution of purified lymphotoxin was placed in microtiter wells and permitted to coat the wells with about 100 ng of lymphotoxin each. The unadsorbed lymphotoxin solution was aspirated from the wells. 50 μl of appropriately diluted test sample was combined with 100 μl PBS containing 5 mg/ml bovine serum albumin (PBS-BSA buffer) and added to each well, incubated for 2 hours at room temperature, washed with PBS containing 0.05 percent Tween 20, 100 μl of horse radish peroidase-labelled goat anti-mouse IgG in PBS-BSA buffer added to each well and incubated for 1 hour. Each well was washed With PBS containing 0.05 percent Tween 20 and then citrate phosphate buffer, pH5, containing 0.1 mg o-phenylene diamine/ml (substrate solution) and aqueous 30 percent $H_2O_2$ (at a proportion of 4 μl of 30 percent v/v $H_2O_2$ per 10 ml of substrate solution) was added to each well. The wells were incubated for 30 min., the reaction stopped with 50 μl 2.5M sulfuric acid and adsorbance measured at 492 nm. Wells which showed adsorbance greater than 1 O.D. were considered anti-lymphotoxin positive.

Test samples also were assayed for the ability to neutralize the cytolytic activity of lymphotoxin in the murine L929 assay. Serum harvested from immunized animals or hybridoma supernatants were diluted as required into RPMI-1640 medium containing 10 percent fetal bovine serum and about 100 lymphotoxin units/ml and plated into microtiter wells containing cultured L929 cells as is otherwise conventional in the cytolysis assay. In the control, all cells were lysed. Neutralizing antibody was detected by failure of the lymphotoxin to lyse L929 cells.

The animal immunized with glutaraldehyde-polymerized lymphotoxin raised antibodies which were active in the ELISA assay, but no serum neutralizing activity was detected.

A suspension containing 100 µg lymphotoxin and 1 ml of a 1.64 percent w/v suspension of aluminum hydroxide [(Al(OH)$_3$] was prepared and used to immunize the same mouse. The mouse was injected with 100 µl of the suspension intramuscularly and 400 µl intraperitoneally. After one week the mouse was injected intravenously with 10 µg of unpolymerized and unadsorbed lymphoblastoid lymphotoxin in 100 µl of PBS. A test of a 1/80 dilution of the animal's serum three days later indicated the presence lymphotoxin neutralizing antibody.

The spleen from this animal was harvested. $3 \times 10^7$ spleen cells were fused with $5 \times 10^7$ murine myeloma cells and plated into microtiter wells containing HAT medium and about 3000 peritoneal macrophages/microtiter well according to the procedure of S. Fazekas De St. Groth, 1980, "J. Immunol. Meth." 35: 1–21. Hybridomas from wells containing supernatants which were positive in the above ELISA assay were grown in 1 ml volume of DMEM medium with 20 percent fetal calf serum, 10 percent NCTC-135 medium, $5 \times 10^{-5}$M beta-mercaptoethanol and HAT, distributed into microtiter wells at a statistical average of one cell per well and then cultured in a 1 or 5 ml volume of the same medium. Supernatants were thereafter assayed for neutralizing antibody. Statistically, about 2 percent of the ELISA positive hybridomas from the aluminum hydroxide immunization synthesized neutralizing antibody. High affinity lymphotoxin antibody optionally is selected from this group of hybridomas.

EXAMPLE 9

Site-Specific Mutagensis of Lymphotoxin

The method of Example 3 is followed exactly in this example except that segment 6 of the synthetic oligonucleotide was modified to have the sequence 5'CTCAACTCT-GCACCCA3' and its complementary strand (segment 53) modified to have the sequence 3'AGACGTGGGTCGTCGT5'.

The modified oligonucleotides are annealed to the remaining oligonucleotides and ligated into the expression vector as described in Example 6. This vector contains a 2 bp substitution which changed the lysine +28 codon from lysine to histidine. The histidine mutant is expressed upon transformation of E. coli ATCC 31446.

Other site-directed mutants are prepared in the same fashion, preferably selecting codons so as to not introduce an EcoRI restriction site that would require the use of a partial EcoRI restriction digest in the digestion of pLTXB1 called for in Example 3. Nor should the mutations introduce additional XbaI or BamHI sites into Fragment A (see FIG. 1b), BamHI or HindIII sites into Fragment B or HindIII or BglII sites into Fragment C. Otherwise, partial digestions will be required to properly assemble the pLTXB1 mutant; digestion to completion would yield a deletion mutant rather than the substitution mutant that is the objective in this case.

EXAMPLE 10

Identification of Genomic DNA Encoding Murine and Bovine Lymphotoxin; Amino Acid Sequence of Murine and Bovine Lymphotoxin The murine and bovine lymphotoxin genes were isolated from genomic-λ libraries. The human lymphotoxin cDNA fragment (PvuII-EcoRI, 600 bp) was radiolabeled with $^{32}P$ by nick translation and used as a probe to screen a murine genomic DNA-λ library (M600 strain murine genomic DNA in λCharon4A, T. Maniatis et al., *Molecular Cloning*, p. 31, 1982) and, independently, a bovine genomic DNA library (EP 88622A). Hybridization was performed at low stringency in 20 percent formamide (Gray and Goeddel "P.N.A.S. USA" 80: 5842–5846 [1983]) and filters were washed twice in an aqueous solution of 0.3M sodium chloride, 0.03M sodium citrate and 0.1 percent SDS. Several phages that hybridized with the human lymphotoxin probe were plaque purified (T. Maniatis et al., "Cell" 15: 687–701 [1978]). Phage DNA was prepared (T. Maniatis et al., "Cell" 15: 687–701 [1978]), digested with restriction endonucleases and analyzed by Southern hybridization. A 3500 bp EcoRI murine DNA fragment and a 2200 bp EcoRI bovine DNA fragment each hybridized with the human lymphotoxin probe. These DNA fragments were subcloned into plasmid pBR322 and then sequenced by the dideoxy chain-termination method (A. J. H. Smith *Methods in Enzymology* 65: 560–580 [1980]). The deduced protein sequence of murine and bovine lymphotoxin, along with that of human lymphotoxin for comparison, is presented in FIGS. 4-I through 4-IV.

EXAMPLE 11

Expression of Lymphotoxin in Yeast Under the Control of the ADH Promoter

Plasmid pLTtrp1 is digested with XbaI in order to open the plasmid at the Xba1 site just proximal to the lymphotoxin start codon. The Xba1 cohesive terminii are blunted by the Klenow fragment of *E. coli* DNA polymerase I with four dNTPs. An EcoR1 adaptor

OH
5' AATTCCCGGG 3'
GGGCCC—P 5'
3' OH is ligated to the blunted plasmid fragment, the protruding 5' hydroxyl termini phosphorylated using polynucleotide kinase, the ligation mixture used to transform *E. coli* ATCC 31446 and a plasmid pLTtrp1R1 identified by restriction analysis that contains an additional EcoR1 site proximal to the lymphotoxin start codon. Plasmid pLTtrp1R1 is isolated, digested with EcoR1 and the lymphotoxin DNA-containing fragment SP recovered.

Plasmid pFRPn (EP 60,057A) is digested with EcoR1, treated with alkaline phosphatase to prevent recircularization, ligated to the SP lymphotoxin fragment using T4 DNA ligase and the ligation mixture then used to transform *E. coli* ATCC 31,446. Ampicillin resistant colonies yield two series of plasmids having the SP insert in opposite orientations as determined by restriction analysis on agarose electrophoresis gels. Plasmids are purified from *E. coli* transformants and used to transform yeast having the trp1 mutation (for example yeast strain RH218, unrestricted ATCC deposit No. 44076) to the $trp^+$ phenotype. Plasmids oriented such that the start codon of segment SP is located adjacent to the alcohol dehydrogenase promoter fragment are found to transform the yeast to lymphotoxin expression. Lymphotoxin is recovered from extracts of the yeast transformants. The plasmid stability in large scale fermentations can be improved by employing an expression plasmid containing the 2 micron origin of replication in place of the pFRPn chromosomal origin of replication (ars 1) and a compatible host strain (J. Beggs, 1978, "Nature" 275: 104–109).

EXAMPLE 12

Expression of Lymphotoxin in Mammalian Cells

λLT11 (Example 2) is digested with EcoR1 and the lymphotoxin-containing DNA fragment (the reverse transcript) recovered. Plasmid pEHER (EP 117,060A) is digested with EcoR1, treated with calf intestinal alkaline phosphatase, and ligated to the EcoR1-linkered reverse transcript of λLT11. The resulting plasmids grown on *E. coli* ATCC 31446 (EP 117,060A) and designated pEHERLT I and pEHERLT II. They contained the lymphotoxin DNA in opposite orientations as determined by restriction analysis on polyacrylamide gels. These plasmids are used to transfect and select CHO DHFR-DUX-B11, CHO 1 and $Ltk^-$cells.

Tissue culture cells are transfected by mixing 1 μg of pEHERLT I or pEHERLT II as prepared above with 10 μg rat carrier DNA in a volume of 250 μl, 0.25M $CaCl_2$, followed by dropwise addition of 250 μl HEPES buffered saline (280 mM MACl, 1.5 mM $Na_2PO_4$, 50 mM HEPES, pH 7.1). After 30 minutes at room temperature, the solution is added to tissue culture cells growing in 60 mm plastic tissue culture dishes. CHO 1, CHO DHFR-DUX-B11, and $Ltk^-$cells are used. The dishes contain 3 ml culture medium appropriate to the host cell.

For CHO 1 and CHO DHFR-DUX-B11 cells, the medium is Ham F-12 media (Gibco) supplemented with 10 percent calf serum, 100 μ/ml penicillin 100 μg/ml streptomycin, and 2 μmM L-glutamine. For the $Ltk^-$cell line, the medium is Dulbecco modified Eagle's medium (DMEM) supplemented as above.

After 3–16 hours, the medium is removed and the cells are washed with 20 percent glycerol in phosphate buffered saline. Fresh medium is added to each plate and the cells are incubated for 2 more days.

Selection of transfected host cells is carried out by trypsinizing the cells after 2 days growth (which comprises treating the cells with sterile trypsin 0.5 mg/ml containing 0.2 mg/ml EDTA) and adding about $3\times10^5$ cells to 10 mm tissue culture plates with selective media. For $dhfr^-$cells the medium is a formulation of (F-12 GIBCO) medium lacking glycine, hypoxanthine, and thymidine ($GHT^-$ medium). For $DHFR^+$ host cells, methotrexate (100–1000 nM) is added to the normal growth medium. Controls are run using transfection conditions with no plasmid and with plasmid pFD-11 (EP 117,060A) containing normal DHFR. Colonies arising from cells which take up and express the DHFR plasmid are apparent within 1–2 weeks. Transformants are identified that express mature lymphotoxin.

We claim:

1. A substantially homogeneous, biologically active human lymphotoxin species comprising at least residues His+24 to Leu+171 of the amino acid sequence of FIGS. 2A-I and 2A-II, which is unglycosylated.

2. The lymphotoxin of claim 1 having specific activity of about from $2\times10^7$ units/mg to about $10\times10^7$ units/mg of protein.

3. The lymphotoxin of claim 1 having a signal or leader polypeptide at the amino terminus of the lymphotoxin species.

4. The lymphotoxin of claim 1 comprising at least residues Leu+1 to Leu+171 of the amino acid sequence of FIGS. 2A-I and 2A-II and having a methionyl or formyl methionyl group attached to residue Leu+1.

5. The lymphotoxin of claim 1 comprising at least residues Met-34 to Leu+171 of the amino acid sequence of FIGS. 2A-I and 2A-II.

6. The lymphotoxin of claim 1 comprising at least residues Leu+1 to Leu+171 of the amino acid sequence of FIGS. 2A-I and 2A-II.

7. The lymphotoxin of claim 6 in aggregate form.

8. The lymphotoxin of claim 1 having a methionyl or a formyl methionyl group attached to residue Kis+24.

9. The lymphotoxin of claim 1 in aggregate form.

10. The lymphotoxin of claim 1 wherein said lymphotoxin is the product of a prokaryotic expression system.

11. The lymphotoxin of claim 10 which is the product of an *E. coli* expression system.

12. A substantially homogeneous, biologically active lymphotoxin species consisting of residues His+24 to Leu+171 of the amino acid sequence of FIGS. 2A-I and 2A-II, which is unglycosylated.

13. The lymphotoxin of claim 12 having a methionyl or a formyl methionyl group attached to residue His+24.

14. The lymphotoxin of claim 12 wherein said lymphotoxin is the product of a prokaryotic expression system.

15. The lymphotoxin of claim 14 which is the product of an *E. coli* expression system.

16. A substantially homogeneous, biologically active lymphotoxin species consisting of residues Leu+1 to Leu+171 of the amino acid sequence of FIGS. 2A-I and 2A-II, which is unglycosylated.

17. The lymphotoxin of claim 16 having a methionyl or a formyl methionyl group attached to residue Leu+1.

18. The lymphotoxin of claim 16 wherein said lymphotoxin is the product of a prokaryotic expression system.

19. The lymphotoxin of claim 18 which is the product of an *E. coli* expression system.

20. A therapeutic composition comprising the lymphotoxin of claim 1 or claim 12 and a physiologically acceptable stabilizer or excipient.

21. An article of manufacture comprising a vial which contains a composition according to claim 20 in sterile form.

22. A therapeutic composition comprising the lymphotoxin of claim 6 or claim 16 and a physiologically acceptable stabilizer or excipient.

23. An article of manufacture comprising a vial which contains a composition according to claim 22 in sterile form.

* * * * *